United States Patent
Putnam et al.

(10) Patent No.: US 8,173,438 B1
(45) Date of Patent: May 8, 2012

(54) MICROBIOLOGICAL ASSESSMENT METHOD AND DEVICE UTILIZING OXYGEN GRADIENT SENSING

(75) Inventors: David L. Putnam, Sammamish, WA (US); Todd W. Hubbard, Seattle, WA (US); Gamal E. Khalil, Redmond, WA (US)

(73) Assignee: Photonic BioSystems, Inc., Sammamish, WA (US)

( * ) Notice: Subject to any disclaimer, the term of this patent is extended or adjusted under 35 U.S.C. 154(b) by 0 days.

(21) Appl. No.: 08/946,823

(22) Filed: Oct. 8, 1997

Related U.S. Application Data

(63) Continuation of application No. 08/729,805, filed on Oct. 8, 1996, now abandoned.

(51) Int. Cl.
G01N 33/00 (2006.01)
G01N 21/76 (2006.01)
C12Q 1/02 (2006.01)
C12Q 1/18 (2006.01)

(52) U.S. Cl. ............. 436/138; 436/172; 435/29; 435/32

(58) Field of Classification Search .................. 436/138, 436/172; 435/29, 32
See application file for complete search history.

(56) References Cited

U.S. PATENT DOCUMENTS

| | | | |
|---|---|---|---|
| 2,879,207 A | 3/1959 | Poitras | |
| 3,107,204 A | 10/1963 | Brown | |
| 3,661,717 A | 5/1972 | Nelson | |
| 3,881,993 A | 5/1975 | Freake | |
| 4,291,122 A | 9/1981 | Orelski | |
| 5,173,432 A * | 12/1992 | Lefkowitz et al. | 436/138 |
| 5,308,581 A * | 5/1994 | Lippitsch et al. | 422/82.08 |
| 5,567,598 A | 10/1996 | Stitt | |
| 6,395,506 B1 | 5/2002 | Pitner | |
| 2002/0192636 A1* | 12/2002 | Guarino et al. | 435/4 |
| 2004/0106209 A1* | 6/2004 | Keith | 436/127 |

FOREIGN PATENT DOCUMENTS

| | | |
|---|---|---|
| AU | 777812 | 2/2005 |
| AU | 2005200504 | 10/2008 |
| EP | 0509791 | 10/1992 |
| EP | 0934428 | 1/2004 |
| WO | WO 95/16052 | 6/1995 |
| WO | WO 98/15645 | 4/1998 |

OTHER PUBLICATIONS

Backman et al., "Cell growth experiments using a microcalorimetric vessel equipped with oxygen and pH electrodes," Journal of Biochemical and Biophysical Methods, 1991, pp. 283-293, vol. 23.

Li et al., "Scanning optical sensor for the measurement of dissolved oxygen and BOD," Sensors and Actuators B, 1994, pp. 143-149, vol. 21.

* cited by examiner

*Primary Examiner* — Rosanne Kosson
(74) *Attorney, Agent, or Firm* — Barry L. Davison; Davis Wright Tremaine LLP

(57) ABSTRACT

There is disclosed a biological indicator (BI) test utilizing oxygen sensing within a microenvironment as a means for determining the presence of viable microorganisms capable of growth, a method for biological indicator (BI) testing for determining the completeness of a sterilization cycle utilizing oxygen sensing as the means for determining the presence of viable microorganism survival, a device for determining oxygen content in a biological indicator (BI) assay vessel containing an optical oxygen sensor, and a method and device for determining antimicrobial drug resistance or sensitivity to a contaminated sample.

37 Claims, 13 Drawing Sheets

Panel B

Panel A

MICROBIOLOGICAL ASSESSMENT METHOD AND DEVICE UTILIZING OXYGEN GRADIENT SENSING

CROSS-REFERENCE TO RELATED APPLICATIONS

This application claims the benefit of priority to U.S. patent application Ser. No. 08/729,805 filed Oct. 8, 1996 and entitled "MICROBIOLOGICAL ASSESSMENT METHOD AND DEVICE UTILIZING OXYGEN GRADIENT SENSING," incorporated by reference herein in its entirety.

TECHNICAL FIELD OF THE INVENTION

The present invention provides a device and process for rapid assessment of microbiological viability of very small amounts of microorganisms by local oxygen sensing of oxygen gradients in a microenvironment having both a luminescent oxygen sensor and the microorganisms in close proximity. The inventive device and process has utility for more rapid testing of microbiological growth and metabolism and has utility for multiple applications, including, for example, biological indicator testing, drug resistance or sensitivity testing, microbiological contamination of tissues and environmental samples, and biological oxygen demand (BOD) testing of water samples.

BACKGROUND OF THE INVENTION

Microbiological testing for microbial growth and metabolism often takes on many forms, including biological indicator (BI) testing (e.g., sterility testing), biological oxygen demand (BOD) testing, and antibiotic drug resistance/sensitivity testing of infections. Although processes exist for all three kinds of microbial testing, such processes usually involve long incubation times for whatever microorganisms are present in a particular sample to grow out enough to be noticed by visual detection systems. Thus, the answer to each question, regarding the degree of contamination for BOD testing, or if sterilization has effectively eliminated viable microorganisms in BI testing, or if a particular strain of infectious microorganism will be killed by a particular drug, each take long time periods of up to about 48 hours to provide test results. There is a tremendous need in the art to conduct such tests and obtain results much faster. The present invention is designed to provide inventive tests, integrated sensor materials, testing apparatus, and methods designed to increase the speed of such tests by utilizing oxygen sensing measurements in a controlled microenvironment.

Medical procedures worldwide often require sterile environments, equipment, apparatus and devices to prevent patient infection. While disposable or "single use" equipment can be packaged and used under sterile conditions, reusable equipment, apparatus and devices (e.g., surgical tools) require thorough washing and sterilization prior to each use. The assurance of an adequate sterilization cycle is critical in the prevention of infection and the spread of diseases. Furthermore, before using instrumentation in surgical and dental procedures, personnel need to know if the instruments have been properly sterilized, as close to completion of the sterilization as possible. Unfortunately, conventional tests for sterility assurance require a lengthy time and subjective observations before the sufficiency of the process can be evaluated.

A biological indicator (BI) testing device can be included in a sterilization run, but typically the sensing element consists of bacteria that must be grown in culture media at an elevated temperature for a period of days before the adequacy of the sterilization can be determined. The viability of any bacteria remaining after the sterilization is determined by measuring bacterial growth or metabolic byproducts. If there is no growth, then the sterilization cycle was effective and the bacteria adequately destroyed. If growth occurs, then the sterilization cycle was faulty or incomplete. There is a need in the art to find this answer as quickly and reliably as possible.

Most of the conventional growth tests are conducted at test facilities outside the medical or dental offices, which can add to delay and cost in obtaining the results. Further, extraneous bacteria may be inadvertently introduced into the test during handling, thereby increasing the chances for incorrect results. Often, the instruments contained within a particular sterilization cycle cannot be quarantined and must be used at risk before the results of a particular growth test are known. Therefore, it is desirable to determine the results of a sterilization cycle within a short period of time, such that the sterility of the instruments sterilized is known before their use on a patient.

BI tests have been developed which reduce the handling requirements and thereby decrease the risk for inadvertent contamination. Other improvements include the use of a pH dye in the growth media which changes color to indicate spore growth. Thus, "self-contained BI's" which permit a biological sample to be exposed to a sterilizing environment (along with the desired articles to be sterilized) with the unit subsequently providing a means of sealing and immersing the biological sample in a growth-inducing medium upon activation of the unit are one example. The inclusion of indicator dyes in the growth medium help provide a more easily observable measure of bacterial growth than simple turbidity changes. These improvements still require long incubation periods, frequent observation of the BI and significant user training to differentiate the color change to expect upon growth.

There are commercially-available chemical indicators which indicate sterility by a color change or a change from a liquid or solid state. Although the results are known immediately after the sterilization cycle, the results are based upon the fact that a particular temperature has been reached or that ethylene oxide gas was present during the sterilization cycle. So called "sterilization integrators" are similarly limited to measuring only a few sterilization parameters. Even the fluorescent enzyme inactivation tests recently introduced do not adequately reflect the complexity of the sterilization process. In the art and by statute, it is generally recognized that only tests utilizing intact, live organisms adequately integrate the chemical and physical parameters necessary to affect sterilization.

Accepted methods for sterility assurance testing involve biological indicator (BI) tests based upon killing a well characterized, defined population of organisms during the sterilization process. Detection of organism growth, i.e. sterilization failure, is often visual wherein a test sample containing viable microorganisms is placed into the sterilizer and after completion of sterilization, the test sample is incubated with growth media for up to 7 days and "read" for evidence of microorganism growth indicated by changes in turbidity or subtle color changes in the media. More commonly now, a colorimetric pH indicator is added such as phenol red or bromthymol-blue to help in detecting a metabolic process occurring.

The shortcoming of these BI tests is reflected in the long times required to make the determination of metabolic activity. Visualizing turbidity requires relatively long optical path lengths to achieve sufficient opacity for viewing, necessitating large media volumes, and are highly subjective during the early grow out period. Optical detection of pH changes with pH indicators similarly requires relatively long path lengths and additionally must overcome the high pH buffering of biological media. These constraints on conventional BI tests lead to long times to confirmation of test results and necessitates that most equipment be used at risk.

Therefore, there is a need in the art to improve upon BI test methodologies to provide more sensitive testing procedures and devices and to provide for earlier readouts of the test results. The present invention addresses these needs in the art.

When patients have an infection, often times the infectious agent is found within blood or other tissue samples. Such bacterial infections are serious and life-threatening and require effective treatment as soon as possible. Current procedures involve culturing blood or tissue samples to identify the presence of the organisms. Further identification of the isolated organism requires biochemical tests and antimicrobial sensitivity/resistance tests to determine effective treatments. In one method, the isolated organism is plated in a confluent layer on appropriate agar plates with small paper disks, each containing a different antibiotic. This culture test looks for area of clear media (absence of bacterial organism) in an otherwise cloudy lawn of bacterial growth to find that drug or those drugs likely to be effective in combating the infection. Unfortunately, the culture test for resistance/sensitivity takes up to 24 hours to perform and patients require treatment to be initiated much sooner. Therefore, the medical practitioner will prescribe broad spectrum antimicrobial to treat likely cause of the bacturemia. Microbial insensitivity to the antibiotic agent will require reevaluation of treatment options, patient retrieval and further monitoring for clinical progress. The present invention was made to apply oxygen sensing technology developed in a microenvironment in BI testing to drug resistance/sensitivity testing of many potential therapeutic agents.

SUMMARY OF THE INVENTION

The present invention provides an integrated sensor component, useful for BI testing or drug resistance/sensitivity testing, comprising a solid matrix containing within or layered on, a solid phase luminescent oxygen sensor and microorganisms, and optionally containing a potential antimicrobial drug, wherein the solid phase luminescent oxygen sensor comprises a luminescent oxygen sensor dye within a polymeric carrier. Preferably the luminescent oxygen sensor dye is selected from the group consisting of polycyclic aromatic hydrocarbons (i.e., pyrene, pyrenebutyric acid, fluoranthene, decacylene, diphenylanthracene, and benzo(g,h,I)perylene) longwave absorbing dyes (i.e., perylene dibutyrate), heterocycles (i.e., fluorescent yellow and tyrpaflavin), porphyrins (i.e., platinum or palladium octaethylporphyrin, tetraphenylporphyrin, tetrabenzoporphrin, chlorins, bacteriochlorins, isobacteriochlorins and chlorophyll), ruthenium(II)tris(bipyridyl) complexes, osmium (II)tris(bathophenanthroline) complexes, and combinations thereof. Preferably, the solid matrix is a porous material, selected from the group consisting of cellulosic materials, mixed cellulose esters, isopore polycarbonate or polyester membranes, nylon filter nets, woven polypropylene, expanded PTFE membranes, glass fiber filter, filter paper, and combinations thereof. Preferably, the polymeric carrier is selected from the group consisting of polycarbonate, silicon, polymethyl methacrylate, polystyrene, polyvinylchloride, alpha-methyl styrene, and combinations thereof.

The present invention provides a method for rapidly assessing oxygen metabolism of a sample of microorganisms contained within a fluid or medium, in which microorganisms create a surrounding oxygen gradient, comprising:

(a) placing a solid phase luminescent oxygen sensor within the surrounding oxygen gradient, wherein the solid phase luminescent sensor comprises a luminescent oxygen sensor dye within a polymeric carrier;

(b) irradiating the solid phase luminescent oxygen sensor to create a returned luminescent signal; and (c) measuring and processing the returned luminescent signal into a measure of relative oxygen concentration within the surrounding oxygen gradient. Preferably, the surrounding oxygen gradient comprises a gradient of reduced oxygen tension within the fluid or medium surrounding the microorganisms. Preferably, the sample of microorganisms is contained within a solid matrix component (sometimes called a "Dual Biological Sensor" or DBS). Preferably the solid matrix component further comprises the solid phase luminescent oxygen sensor. This is called an "integrated biological sensor" or IBS.

The invention further provides various applications of the foregoing inventive integrated sensor component and method for rapidly assessing oxygen metabolism of a sample of microorganisms contained within a fluid or medium, which applications are biological indicator (BI) testing, anti-microbial drug resistance/sensitivity testing, and general viable microbial activity testing.

The present invention provides a biological indicator (BI) test device, comprising a vessel having internal contents and a means for forming a barrier to external contamination of the vessel internal contents, wherein a portion of the vessel provides a means for optical interrogation of the internal contents of the vessel, wherein the internal contents of the vessel comprise a solid phase luminescent oxygen sensor, viable microorganisms capable of growth and oxygen consumption, and growth media capable of sustaining growth of the organisms and containing measurable quantities of oxygen, wherein the solid phase luminescent oxygen sensor comprises a luminescent oxygen sensing dye in a polymer carrier. Preferably, the solid phase luminescent oxygen sensor is contained within or on the surface of a solid matrix. Most preferably, the microorganisms are also contained within or on the surface of the solid matrix. Preferably, the viable microorganisms comprise bacterial spores. Most preferably, the bacterial spores are *B. stearothermophilus* or *B. subtilis* or combinations thereof, for sterility assurance testing. Preferably, the microorganisms are provided within the vessel fixed onto a solid matrix. Preferably the solid matrix is selected from the group consisting of cellulosic materials, mixed cellulose esters, isopore polycarbonate or polyester membranes, nylon filter nets, woven polypropylene, expanded PTFE membranes, glass fiber filter, filter paper, and combinations thereof. Preferably, the polymeric carrier is selected from the group consisting of polycarbonate, silicon, polymethyl methacrylate, polystyrene, polyvinylchloride, alpha-methyl styrene, and combinations thereof. Preferably, the luminescent oxygen sensing dye is selected from the group consisting of polycyclic aromatic hydrocarbons (i.e., pyrene, pyrenebutyric acid, fluoranthene, decacylene, diphenylanthracene, and benzo(g,h,I)perylene) longwave absorbing dyes (i.e., perylene dibutyrate), heterocycles (i.e., fluorescent yellow and tyrpaflavin), porphyrins (i.e., platinum or palladium octaethylporphyrin, tetraphenylporphyrin, tetrabenzoporphrin, chlorins, bacteriochlorins, isobacteriochlorins and chlorophyll), ruthenium(II)tris(bipyridyl) complexes, osmium (II)tris(bathophenanthroline) complexes, and combinations thereof. Preferably, the BI test device further provides a means for providing a physical or chemical barrier to retard ingress of oxygen to the microorganisms. Preferably, the growth media is contained within an enclosed glass vessel that can be broken to deliver growth media to the microorganisms.

The present invention further provides a method for biological indicator (BI) testing for determining the effectiveness of a sterilization cycle, comprising:

(a) exposing a biological indicator test device to a sterilization cycle, wherein the BI test device comprises a vessel having internal contents and a means for forming a barrier to external contamination of the vessel internal contents, wherein a portion of the vessel provides a means for optical interrogation of the internal contents of the vessel, wherein the internal contents of the vessel comprise a solid phase luminescent oxygen sensor, viable microorganisms capable of growth and oxygen consumption, and growth media capable of sustaining growth of the organisms and containing measurable quantities of oxygen, wherein the solid phase luminescent oxygen sensor comprises a luminescent oxygen sensing dye in a polymer carrier;

(b) exposing the microorganisms to the growth media, and incubating the biological indicator test device under incubation conditions optimal for growth of the microorganisms; and (c) determining oxygen consumption within the BI test device, over a time interval, wherein evidence of oxygen consumption indicates the presence of surviving microorganisms and incomplete sterilization.

Preferably, the time for incubation is at least 20 minutes but no longer than 16 hours under optimal growth conditions for the sample of microorganisms provided.

The present invention further provides a drug resistance/sensitivity test device for rapidly determining if a sample of microorganisms are resistant or sensitive to a potential antimicrobial therapeutic agent, comprising a plurality of porous solid matrix elements, each containing a solid phase luminescent oxygen sensor, and potentially contaminated sample applied to a solid matrix element; and a test vessel containing a solid matrix element, growth media, and optionally a potential antimicrobial therapeutic agent, wherein the porous solid matrix element is an absorbent or filtering device. Preferably, the porous solid matrix element is selected from the group consisting of cellulosic materials, mixed cellulose esters, isopore polycarbonate or polyester membranes, nylon filter nets, woven polypropylene, expanded PTFE membranes, glass fiber filter, filter paper, and combinations thereof.

The present invention further provides a method for antimicrobial agent resistance/sensitivity testing of a potentially contaminated sample, comprising:

(a) providing a drug resistance/sensitivity test device, wherein the drug resistance/sensitivity test device comprises a plurality of porous solid matrix elements, each containing a solid phase luminescent oxygen sensor, wherein the porous solid matrix element is an absorbent or filtering device;

(b) administering the potentially contaminated sample to the porous solid matrix elements;

(c) placing one porous solid matrix element in each test vessel containing growth media and optionally containing a potential antimicrobial therapeutic agent;

(d) incubating each test vessel under conditions optimal for microbial growth; and (e) determining oxygen consumption within the test vessel, over a time interval, wherein evidence of oxygen consumption indicates the presence of viable microorganisms and antimicrobial drug resistance.

The present invention further provides a microbial activity test device for rapidly determining microbial activity in a filtered sample of microorganisms, comprising a porous solid matrix element, containing a solid phase luminescent oxygen sensor, and potentially contaminated sample filtered through the solid matrix element; and a test vessel containing the solid matrix element and growth media, wherein the porous solid matrix element is an absorbent or filtering device. Preferably, the porous solid matrix element is selected from the group consisting of cellulosic materials, mixed cellulose esters, isopore polycarbonate or polyester membranes, nylon filter nets, woven polypropylene, expanded PTFE membranes, glass fiber filter, filter paper, and combinations thereof.

The present invention further provides a method for determining microbial activity in a potentially contaminated sample, comprising:

(a) providing a microbial activity test device, wherein the microbial activity test device comprises a porous solid matrix element, containing a solid phase luminescent oxygen sensor, wherein the porous solid matrix element is an absorbent or filtering device;

(b) filtering the potentially contaminated sample through the porous solid matrix element;

(c) placing one porous solid matrix element in each test vessel containing growth media;

(d) incubating the test vessel under conditions optimal for microbial growth; and (e) determining oxygen consumption within the test vessel, over a time interval, wherein evidence of oxygen consumption indicates the presence of viable microorganisms.

The present invention further provides a optical-assay system for determining oxygen content in a vessel, comprising:

(a) a solid phase luminescent oxygen sensor bound to a solid matrix and contained within a testing vessel, wherein the solid phase luminescent oxygen sensor comprises a luminescent oxygen sensing dye within a polymer carrier, and, when irradiated with light of an appropriate wavelength, generates a returned luminescent signal;

(b) a light source that irradiates the solid phase luminescent oxygen sensor;

(c) a photodetector device that monitors the returned luminescent signal and processes the returned signal into a measure of relative oxygen concentration; and (d) a means for transmitting irradiating light to the solid phase luminescent oxygen sensor and for transmitting the returned signal from the solid phase luminescent oxygen sensor to the photodetector device. Preferably, the optical assay system is used for BOD (biological oxygen demand) testing, providing that contents in the vessel are mixed. Preferably, the solid phase luminescent oxygen sensor is affixed to a cap of a BOD testing vessel.

BRIEF DESCRIPTION OF THE FIGURES

FIG. 2 shows a preferred embodiment of the inventive BI vessel using a glass culture tube and a sensor tube integrated into the sensor cap to reduce volume in the assay chamber. The sensor membrane is in direct contact with growth media in the assay chamber and the device is read by external interrogation with a fiber bundle through a wall of the sensor tube.

DETAILED DESCRIPTION OF THE INVENTION

Figure 1:
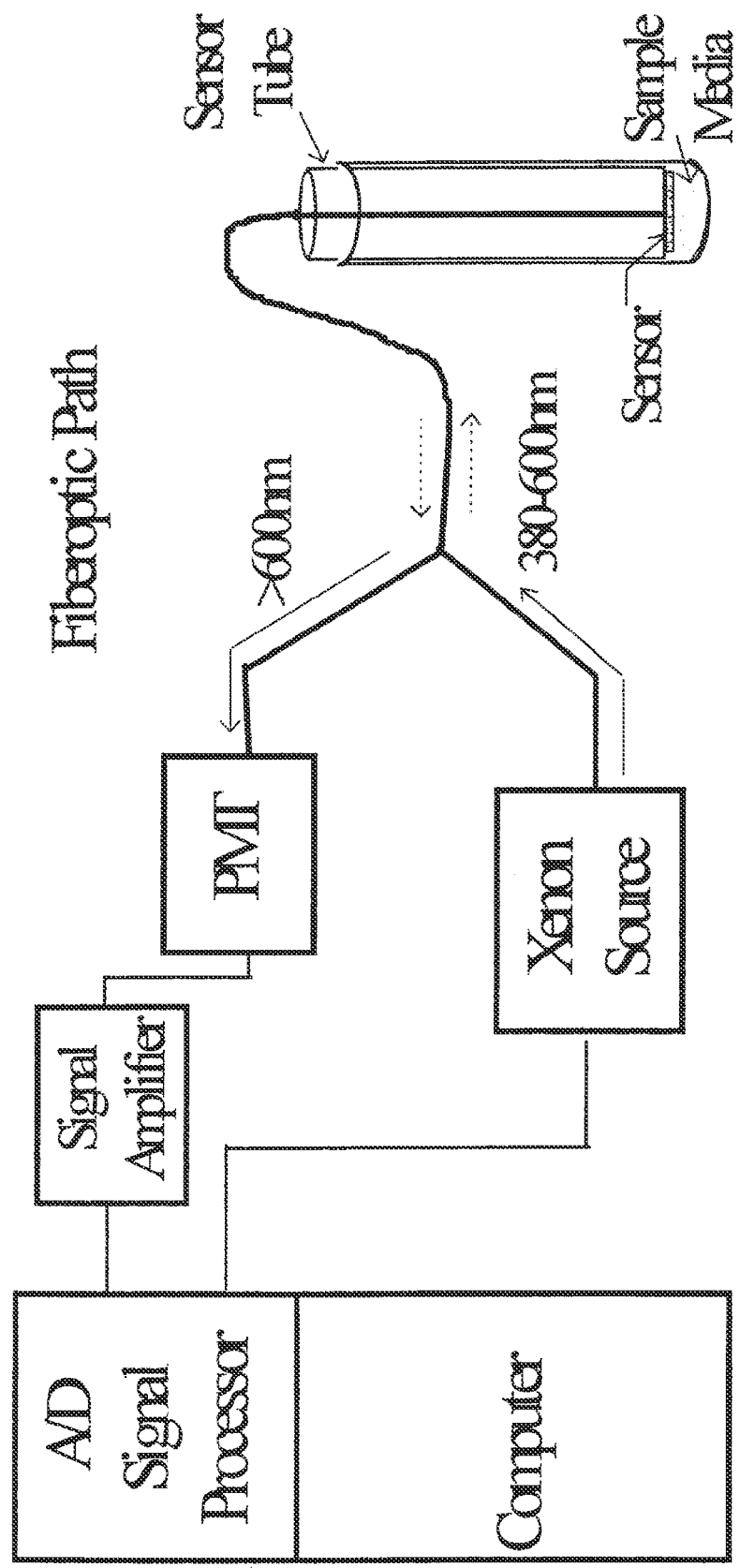
FIG. 1 shows a schematic of opto-electronics in a preferred optical signal sensing means. The illustrated opto-electronics interrogates an optical oxygen sensor sealed inside a vessel. In this opto-electronics scheme, a computer serves as a platform from which the opto-electronics are controlled and returned signals are acquired and analyzed. The computer triggers a xenon-flash source (light source that irradiates optical oxygen sensor) to launch a designated number of excitation light pulses. The flash is optically filtered to encompass excitation bands of the optical oxygen sensor and coupled into one arm of a fiber bundle (means for transmitting irradiated light to the optical oxygen sensor and for transmitting a returned light signal from the optical oxygen sensor). This bifurcated fiber bundle is used to carry light from the flash to the optical oxygen sensor, collect the phosphorescent signal from the optical oxygen sensor and return the optical signal to the photodetector. The detector and data acquisition system (PMT/amplifier & A/D & computer) process the signal and display the dissolved calculated oxygen levels.

The present invention provides a device and method for rapidly testing microbial metabolism, comprising a solid matrix support containing within or layered on, a luminescent oxygen sensitive dye, wherein the luminescent oxygen sensitive dye is located in the oxygen-gradient surrounding the matrix, created by oxygen metabolism of the test microorganisms. The means described has general applicability to determination of microbial activity that includes sterilization biological indicator (BI) testing, microbial activity tests of liquid samples and anti-microbial drug sensitivity testing. The system comprises:

(a) solid-phase luminescent oxygen sensor contained on or in a porous solid-matrix support (b) microorganisms contained on or in the solid-phase luminescent oxygen sensor;

(c) a testing vessel containing microbial growth media, the solid-phase luminescent oxygen sensor and microorganisms;

(d) a frequency or amplitude-modulated light source that provides light excitation of the luminescent oxygen sensitive composition to emit luminescent light;

(e) a device that monitors a returned signal of luminescent light emitted from the solid-phase luminescent oxygen sensor and processes the returned signal into a measure of relative oxygen concentration; and (f) a means for transmitting modulated light to the solid-phase luminescent oxygen sensor and for transmitting luminescent light from the solid-phase luminescent oxygen sensor to the photodetector device.

BI Testing Method

The present invention provides a BI device and method using an optical luminescent oxygen-sensing technique to measure dissolved-oxygen (DO) in solid support matrix containing previously viable microorganisms that have been exposed to sterilizing conditions, said support disk immersed in growth media. In one embodiment, the inventive method employs an luminescent optical oxygen sensor, such as an oxygen-quenchable luminescent dye, on a solid matrix support inside the vessel. The microorganisms are contained on a porous solid-matrix support. The microorganisms surviving the sterilization process will consume oxygen and create an oxygen tension proportional to the distance from the solid-matrix support. This oxygen tension gradient can be sensed by a solid-phase luminescent oxygen sensor brought into this gradient. This BI test configuration with a solid-matrix support containing microorganisms and a separate solid-phase luminescent sensor component is defined as a Dual Biological/Sensor. In another BI test configuration, defined as Integrated Biological/Sensor, the BI device inventively integrates the solid-phase luminescent oxygen sensor and microorganisms into or onto the same solid matrix support and measures the oxygen gradient within the solid-matrix support.

Formation of the oxygen gradient and concomitant changes in the luminescent characteristics of the optical oxygen sensor are measured spectroscopically. An optical instrument externally interrogates the optical oxygen sensor, measuring the luminescence which directly correlates to a measure of oxygen within the gradient around or in the solid-phase luminescent oxygen sensor. Readout is attained via a transparent wall or port without opening the vessel or contacting the sample, thereby enabling monitoring of the vessel contents for evidence of oxygen consumption without breaching the integrity of the vessel and risking contamination of the vessel contents. It is important to note that it is not essential to know what the exact amount of oxygen is within the sample. The assay measures relative optical signal changes in the solid-phase luminescent oxygen sensor, which are dependently related to the oxygen concentration within the gradient around the solid-phase luminescent oxygen sensor. Changes in the optical signal indicate changes in relative oxygen concentration. Thus, measures of a decrease in the relative concentration of oxygen present over time serve as an indicator of microorganism growth and survival of the microorganisms during sterilization.

The process of measuring the relative oxygen concentration and making determinations indicative of growth can be accomplished in several ways: (1) determining that the oxygen within the gradient surrounding the microorganisms in or on the solid-matrix support has changed and reached a certain threshold value; (2) ascertaining that the oxygen is changing at a rate predefined to be indicative of growth; (3) determining that the rate of change in oxygen occurs with an acceleration predefined to be indicative of growth; (4) using other derivatives or mathematical algorithms based on change over time to predict the metabolic activity indicative of growth.

The inventive devices and methods are based upon the principle of oxygen's quenching of phosphorescent emission of optical oxygen sensor dyes, such as several metal porphyrin molecules with different ring structure derivatives. As an example, porphyrin emissions exhibit large Stokes shifts; excitation maxima from ≈390-600 nm and emission maxima >650 nm with emissions generally exhibiting a relatively long phosphorescent decay lifetimes. For several useful porphyrin derivatives, the "natural decay lifetime" (w/o oxygen) ranges from about 100 to 1000 ms. The photo-excited porphyrin is quenched by oxygen in a radiationless process, reducing the emitted luminescent signal's decay lifetime to ≈20 to 100 ms respectively under ambient conditions of temperature and atmospheric pressure thus, giving a large dynamic measurement range. Using both the phosphorescent decay lifetime and large Stokes shift, the oxygen quench-dependent signal is easily quantified by lifetime spectroscopy to obtain a measure of the oxygen concentration in the environment that the dye molecules are exposed to.

Quenching the excited state porphyrin is a non-consumptive process. Thus, the use of the phosphorescent technology allows the assay of very small volumes without analyte consumption. This feature is in direct contrast to conventional electrochemical methods such as the Clark electrode assessment of oxygen. Other features of the solid-phase luminescent oxygen sensor include its relative immunity to the test environment and fouling of the sensor membrane.

Although the preferred method is to use time-resolved measures of luminescent dye's emitted signals, there are allied means of sensing luminescent oxygen sensors optically. Intensity or amplitude of the signal emitted by lumiphore dyes can be used as an alternative to time-based measures of signal.

For a BI test, a BI vessel comprises a vessel with internal contents and having a means for forming a barrier to external contamination of the vessel contents, wherein the internal contents of the vessel comprise an optical oxygen sensor, viable microorganisms, and growth media suitable for growth of the microorganisms. The BI vessel provides an assay chamber, protected from the external environment, in which the surviving microorganisms can be incubated and cultured to grow in growth media. The BI vessel further provides a means for optical interrogation of the internal contents of the vessel for sensing a change (decrease or consumption) of dissolved oxygen in the growth media surrounding the microorganisms contained within the solid-matrix support. It permits external optical interrogation of the solid-phase luminescent oxygen sensor, by transmission of light through the vessel, thereby making the determination as to whether or not the vessel contains viable microorganisms. In the absence of a successful sterilization, viable microorganisms will be able to grow in the growth media, wherein the consumption of oxygen is an indicator of microorganism survival and an invalid sterilization process.

Figure 2:
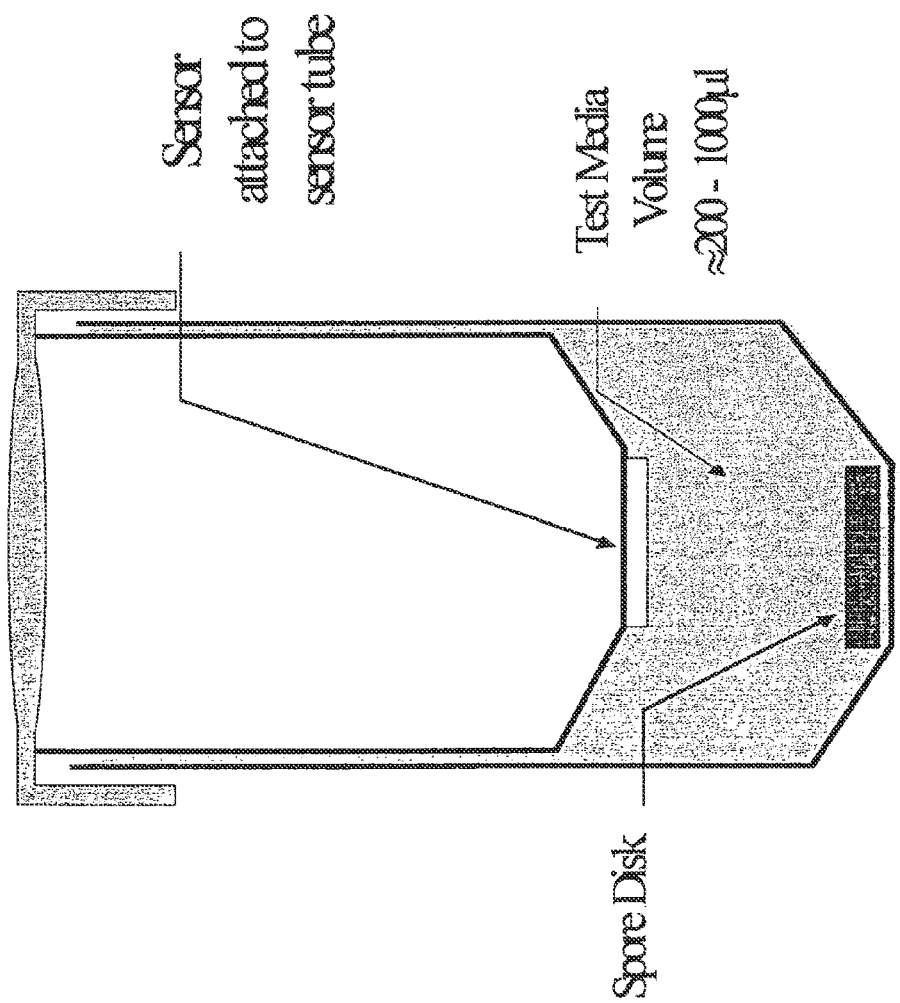
FIG. 2 shows the BI device and vessel having an assay chamber containing media (also containing dissolved oxygen) and microorganisms, a sensor cap, and a phosphorescent sensor membrane attached to the sensor cap and in contact with the media in the assay chamber.
Figure 7:
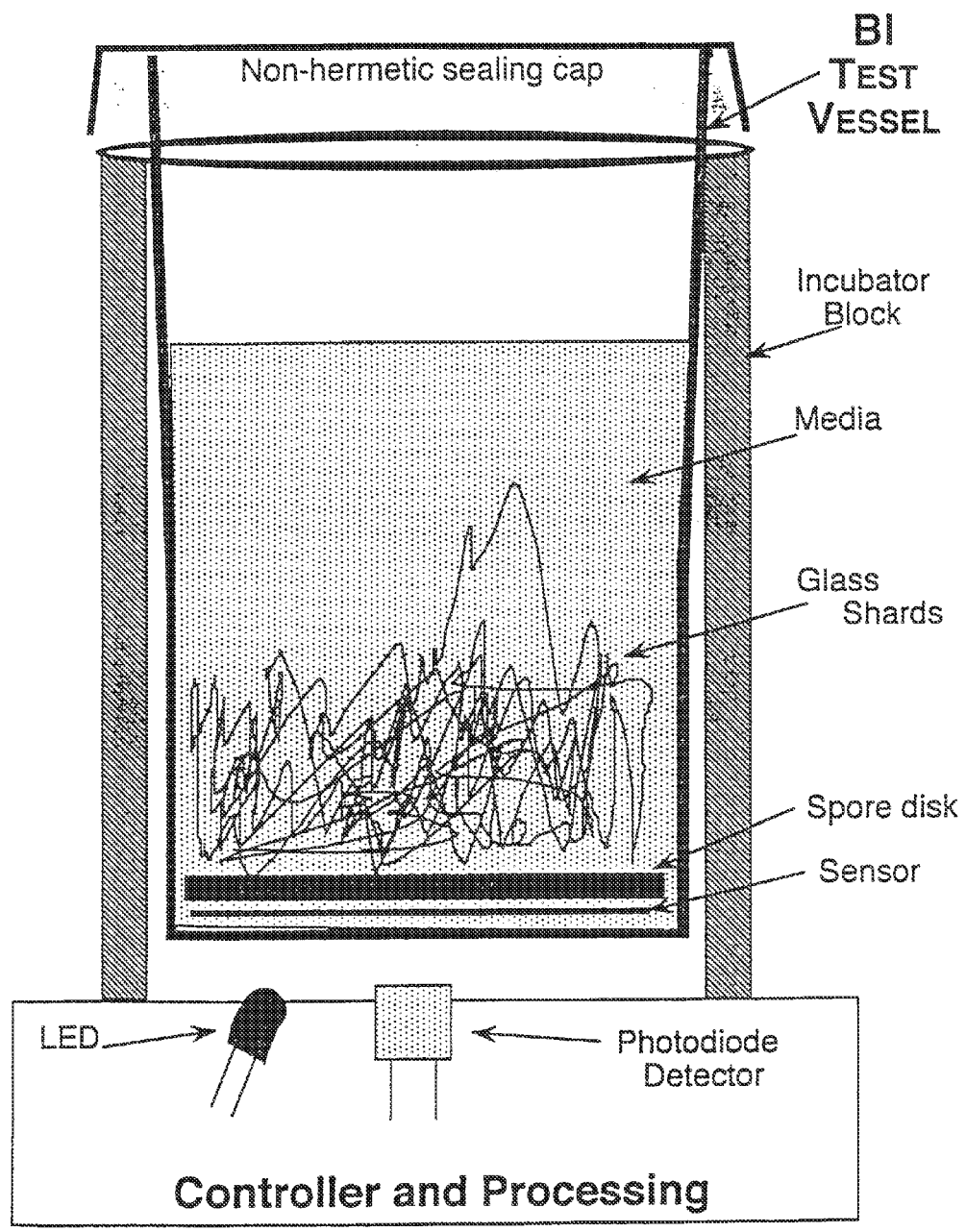
FIG. 7 shows a prototype design of the inventive BI device and assay system. The vessel is shown in the incubator-reader device in a cut-away drawing. The vessel is shown after activation, with the sensor optically readable through the bottom of the vessel, the microorganism sample on a solid matrix carrier substrate (i.e., spore disk) in close proximity with the optical oxygen sensor, and surrounded by the growth media. The glass shards from a broken media ampule are shown overlying the spore disk and optical oxygen sensor. In a preferred embodiment, the total media volume is 1 ml or less with a total column height of fluid greater than 1 cm. Also shown in this preferred embodiment is a vessel closure means providing a tortuous path to the vessel contents, thereby protecting said contents from external microbial contamination.

In addition, the BI vessel permits its contents to be sterilized providing that the sterilization cycle is complete enough to effect full sterilization. In the case of steam, gas, or vaporized sterilization agents, this can be accommodated by providing ports, vents, or a tortuous path which enables the sterilant to penetrate the inner aspects or internal contents of the BI vessel. After sterilization, the BI vessel provides a means for forming a barrier to external contamination of the BI vessel contents. This can be accomplished as simply as providing a loose fitting cap for the vessel (such as depicted in FIGS. 2 and 7).

The solid-phase luminescent oxygen sensor comprises a solid matrix support containing within or layered on, a luminescent oxygen sensitive dye. Preferably the luminescent oxygen sensor dye is selected from the group consisting of polycyclic aromatic hydrocarbons (i.e., pyrene, pyrenebutyric acid, fluoranthene, decacyclene, diphenylanthracene, and benzo(g,h,I)perylene) longwave absorbing dyes (i.e., perylene dibutyrate), heterocyclics (i.e., fluorescent yellow and tyrpaflavin), porphyrins (i.e., platinum or palladium octaethylporphyrin, tetraphenylporphyrin, tetrabenzporphyrin, chlorins, bacteriochlorins, isobacteriochlorins and chlorophyll), ruthenium(II)tris(bipyridyl) complexes, osmium (II) tris(bathophenanthroline) complexes, and combinations thereof.

In one form, the luminescent oxygen sensitive dye is directly adsorbed onto the solid matrix support material creating a stand-alone solid-phase luminescent oxygen sensor. In a second preferred embodiment, a solid-phase luminescent oxygen sensor is made from the oxygen-sensitive dye admixed in a polymeric carrier selected from the group consisting of polycarbonate, silicon, polymethyl methacrylate, polystyrene, polyvinylchloride, polyalpha-methyl styrene, fluorinated polymers or copolymer derivatives and combinations thereof. The admixture is then sprayed or cast onto a solid support to create a stand-alone solid-phase luminescent oxygen sensor. In a third preferred configuration, the luminescent oxygen-sensitive dye and polymer-carrier admixture are physically integrated into or onto the solid-matrix support to create a solid-phase luminescent oxygen sensor. Preferably, the solid matrix support is a porous material selected from cellulosics, mixed cellulose esters, isopore polycarbonate or polyester membranes, nylon filter nets, woven polypropylene, expanded PTFE membranes, and glass fibers mats.

Stand-alone membranes or film preparations of sensors in a preferred means can be prepared by using thin polymer sheets, such as pre-cast polycarbonate isopore films. A suitable solvent is used, such as toluene, which dissolves the luminescent oxygen-sensitive dye and is a weak solvent for the polymer film. The film is exposed to the dye-solvent solution during which the dye partitions to the polymer film. Dye embedded into the matrix remains entrained in the film after the solvent evaporates and the polymer film structure restabilizes. The prepared films constitute one stand-alone form of the solid-phase luminescent oxygen sensor.

The dye impregnated material can then be cut or shaped to the desired sensor dimensions and configuration for the vessel. Standalone sensors are preferably affixed to a solid-matrix support containing the test microorganisms. Alternatively, the stand-alone solid-phase luminescent oxygen sensor can be physically constrained in place within the BI test vessel and the solid matrix support containing the microorganisms can be brought up to the oxygen sensor at a later time. The solid-phase luminescent oxygen sensor is in contact with the growth media in the BI vessel assay chamber, and preferably in close proximity to the solid matrix support containing the microorganisms.

In an alternative format, the admixture of the luminescent oxygen sensitive dye and polymer carrier chosen from the list above, is sprayed and dried directly onto a porous solid matrix support, such as glass fiber mats, to provide reliable and reproducible solid-phase luminescent oxygen sensors.

The solid-phase luminescent oxygen sensor should be made from materials with a high rate of oxygen transfer and equilibration throughout. This results in fast response times to oxygen changes (e.g., 90% of full response attained in <30 sec). The solid-phase luminescent oxygen sensor and solid matrix support materials must also be biocompatible, that is, not having intrinsic anti-microbial characteristics, and that the materials be stable to prolonged exposure to growth media at physiologic or thermophylic temperatures (i.e., 37° C., 56° C.) for periods of time of at least several days. Moreover, the materials must be resistant to sterilization conditions, such as steam, ethylene oxide (EtO), E-beam, hydrogen peroxide vapor ($H_2O_2$) and g-irradiation, and have a shelf life under extreme storage conditions of at least two years.

The microorganisms utilized for the BI assay are preferably of the type approved and accepted for the particular testing purpose. Preferably the microorganisms are prokaryotic microbes. For steam sterilization processes and design of steam sterilization BI's, the preferred microorganism of the currently accepted convention comprises spores of the prokaryotic species *Bacillus stearothermophilus*. For testing ethylene-oxide gas sterilization cycle conditions, the preferred microorganism is spores of the prokaryotic species *Bacillus subtilis*.

Preferably the microorganisms are pre-applied on or in the solid matrix support wherein consumption of oxygen by the microorganisms creates an oxygen-gradient around the solid-matrix support, which can be sensed by a solid-phase luminescent oxygen sensor, placed in the gradient surrounding the solid-matrix. In this configuration with a solid-matrix support containing microorganisms and a separate solid-phase luminescent sensor component are defined as Dual Biological/Sensors. In another preferred configuration, devices integrate the solid-phase luminescent oxygen sensor and microorganisms into or onto the same solid matrix support and measure the oxygen gradient within the solid-matrix support and are defined as Integrated Biological/Sensors.

The BI vessel is, preferably, made from a transparent or translucent polymeric material, such as polycarbonate or polypropylene, which permits optical interrogation of the contents and withstands thermal and chemical conditions associated with steam, EtO or $H_2O_2$ vapor sterilization. Glass is also a desirable vessel material because it is also an effective oxygen barrier material and glass can serve as a substrate onto which an optical oxygen sensor dye/polymer thin film can be applied.

The assay chamber of the BI vessel is the region where microorganisms, growth media containing oxygen, and optical oxygen sensor are confined. It is desirable to reduce influx of oxygen into growth media during incubation. Influx of oxygen will have a counter-productive effect of dampening a measure of oxygen depletion, according to the inventive method. Therefore, one implementation of the inventive device and assay system reduces exposure of growth media to outside air which limits oxygen transfer into the growth media during incubation. Preferably, air is kept out of the assay chamber (e.g., providing air and air bubbles an opportunity to vent out). Preferably, one reduces growth media's exposed surface area to volume ratio. One can also limit growth media's exposure to oxygen by utilizing materials in contact with growth media which have low oxygen content and low oxygen permeability and transfer rates (e.g., gas-barrier materials).

FIGS. 1 and 2 show a schematic of a version of a BI instrument and vessel using oxygen sensing as a means for detecting microorganism growth. FIG. 2 illustrates a vessel assembly constructed using an outer glass culture tube (12× 75 mm) for an assay vessel. Therein a glass sensor tube (10×75 mm) is inserted, which caps and encloses the BI vessel. This configuration also creates a smaller assay volume and confines the microorganisms to a small volume of growth media. The tolerances between the tube walls are sufficiently loose (~0.010") to enable air to be displaced and escape and accommodate excess media, but tight enough that the long narrow path along the walls constitutes an effective barrier to oxygen diffusion. For testing purposes, the depth of insertion of the sensor tube is variable, enabling tests with different assay volumes ranging from ~200 ml to about 2 ml.

In this version, the solid-phase luminescent oxygen sensor is affixed to a bottom face of the BI assay vessel and is in direct contact with growth media during incubation. The BI assay is conducted with the BI device and assay vessel containing growth media and the microorganisms. The microorganism sample (i.e., spores affixed to a paper disk, as shown in the FIG. 2) is located at the bottom of the BI device and assay vessel (i.e., "assay chamber"). FIG. 2 illustrates an assay vessel having a "sensor tube" for controlling assay volume in a withdrawn state, creating an assay chamber of relatively large volume (about 1 ml). By inserting the sensor tube fully, the assay volume is reduced. It is preferable to reduce assay volume as this increases the sensitivity of the assay and decreases the time needed to obtain results, because reduced assay volumes reduce total dissolved oxygen available for microorganism growth, thereby reducing oxygen consumption required to affect a measurable change in oxygen concentration (see example 4 for more details). The longer or more tortuous path between the assay chamber and the outside atmosphere further functions to limit oxygen diffusion into growth media located in the relevant area of the assay chamber (defined as that region of the BI device and assay vessel where the microorganisms and optical oxygen sensor are located). The assay vessel shown is externally optically interrogated with a fiber bundle inserted into the assay vessel (as shown in FIG. 1). This configuration provides a reading of the solid-phase luminescent oxygen sensor through the bottom of the sensor tube.

A preferred self-contained assay vessel configuration is described in U.S. Pat. No. 4,291,122, the disclosure of which is incorporated by reference herein. This vessel consists of a transparent vial containing both a microbial sample and growth media initially separated from the microorganisms. The vessel contains an inner frangible ampule containing the growth media. After completion of the sterilization cycle, the frangible ampule is broken and liquid media is released to come into contact with the microorganisms contained on a paper disk to support growth of surviving microorganisms, as illustrated in FIG. 7. However, this assay vessel configuration make assay volume-limiting means and diffusion barriers more difficult to implement.

An inventive aspect of the BI test device is that it is not essential to seal the microorganisms and optical oxygen sensor in an assay chamber that prevents contact with air or eliminates diffusion paths for oxygen ingress. The microorganisms' high metabolic rate, especially in the case of prokaryotic cells localized onto a solid phase carrier material (e.g., paper), is sufficient to create a gradient of reduced oxygen tension within the growth media. This oxygen gradient extends far enough away from the microorganisms to be measurable by thin film optical oxygen sensors as described herein. By placing the solid-phase optical oxygen sensor close to the microorganisms (i.e., within a "microenvironment" of an oxygen concentration gradient generated by the microorganisms), oxygen consumption by the microorganisms can be detected within this "microenvironment" even if the growth media volume is much larger, provided that the solid-phase luminescent oxygen sensor is located within this "microenvironment".

Growth media, by itself, can act as a barrier to oxygen diffusion, by providing a long diffusion path that adventitiously impedes oxygen from reaching the microenvironment. This long diffusion path is important for microbial activity testing. Additional barriers, such as physical baffles, physical barriers, or chemical agents that increase the viscosity of the growth media, can further reduce diffusion and convection of oxygen. This will improve formation of the oxygen gradient by protecting the microenvironment thereby promoting assay sensitivity. Example 6 (below) shows, for one format of the BI device (Dual Biological/Sensor), evidence of a beneficial effect of reducing diffusion and convection using glass shards as a physical barrier within the growth media.

A preferred embodiment provides that the microorganisms and the optical oxygen sensor are in close proximity to each other. The closer the optical oxygen sensor is to the microorganisms, the greater the assay sensitivity or speed of outgrowth detection. The Integrated Biological/Sensor provides for physical integration of the microorganisms and solid-phase luminescent oxygen sensor into one device, creating a practical and efficient device for increasing assay sensitivity and speed. In a similar light, the volume of growth media exposed to the microorganisms is reduced, such that the amount of oxygen available to the microorganisms is restricted to a small quantity. Thus, the smaller the assay volume (determined by the volume of growth media exposed to the microorganisms), the more rapid the assay answer can be achieved. Thus, the use of smaller assay volumes, the microorganisms and optical oxygen sensor in close proximity, and the use of barriers to oxygen diffusion each help to increase assay sensitivity.

FIG. 7 illustrates the preferred testing mode in which the optical oxygen sensor is in close proximity to the microorganisms. The example is presented in the form of solid-phase luminescent oxygen sensor placed within the oxygen gradient created by the spores fixed onto a solid matrix support (chromatography paper shaped in the form of a disk). FIG. 7 further illustrates an embodiment wherein there is a relatively large volume of growth media, however formation of a microenvironment between the microorganisms and the optical oxygen sensor at the bottom of the assay vessel provides for increased assay sensitivity.

FIG. 1 shows a BI test device for determining the oxygen content inside an assay vessel. In this configuration, a computer is used to control the measurement process and to process and display the results of the assay vessel optical interrogation. A signal from the computer arms an A/D board and triggers a flash tube, which emits a 1-5 W peak pulse of light. A bandpass optical filter and focusing lens couple excitation light into a one arm of a bifurcated fiberoptic cable to the bottom of the assay vessel. The excitation light passes through an optical port in the bottom of the assay vessel, exciting the optical oxygen sensor located within the assay vessel. An amount of luminescent light is emitted from the solid-phase luminescent oxygen sensor in response to the excitation light and in proportion to the amount of dissolved oxygen in the microenvironment surrounding the solid-phase luminescent oxygen sensor. The emitted luminescent light ("returned optical signal") is collected by a second arm of the fiberoptic cable and is returned to a photomultiplier tube (PMT). The returned optical signal is converted to voltage and digitized by an A/D board. Luminescent lifetime of the solid-phase luminescent oxygen sensor signal is calculated by the computer and displayed.

FIG. 7 shows a preferred embodiment of a BI assay system. In this assay system, the excitation light source and PMT are placed within an incubator device and utilize solid state devices located directly below the solid-phase luminescent oxygen sensor means. In a preferred device and method, the solid state light source is an LED, modulated in a series of step pulses of 20 μs to 90 μs in length. The luminescent signal returned from the solid-phase luminescent oxygen sensor is detected by a solid state detector such as a PIN photodiode or avalanche photodiode. As shown, the LED and photodiode detector are built into a heater block which holds the test vessel contents at the desired incubation temperature.

Microenvironment

The present invention is based upon the advantage of determining a small quantity of growing/metabolizing microorganisms that are able to grow in a microenvironment, wherein the microenvironment is in close proximity to a sensor element containing a luminescent oxygen-sensitive dye compound. This is often accomplished by providing an sensor on a solid matrix that will be able to sense changes in oxygen concentrations from metabolizing microorganisms in a closely surrounding microenvironment. The advantage of detecting oxygen respiration in only a close microenvironment is that very small populations of respiring microorganisms can be detected. This results in an ability to obtain an answer to a question (such as a BI test, or antibiotic resistance/sensitivity) more rapidly. The present invention provides a means for reading the optical luminescent sensor element to measure the presence or absence of metabolizing microorganisms in the microenvironment surrounding this element.

Microbial Activity Determination

The present invention further provides a microbial activity test device for rapidly determining microbial activity in a filtered sample of microorganisms, comprising a porous solid matrix element, containing a solid phase luminescent oxygen sensor, and organisms from a contaminated sample filtered through the solid matrix element; and a test vessel containing the solid matrix element and growth media, wherein the porous solid matrix element is an absorbent or filtering device. Preferably, the solid matrix support is a porous material selected from cellulosics, mixed cellulose esters, isopore polycarbonate or polyester membranes, nylon filter nets, woven polypropylene, expanded PTFE membranes, and glass fibers mats.

In a preferred configuration, the solid-phase luminescent oxygen sensor can be used as a filter device for concentration and detection of metabolizing (viable) microorganisms from fluid samples creating an "Integrated Biological/Sensor". Alternatively, the solid-phase luminescent oxygen sensor can be bound to a microbial filtering element (per the Dual Biological/Sensor configuration) for collection of organisms from a fluid sample and subsequent detection of their metabolic activity.

The integrated sensor is designed to function both as a microbial membrane device for capturing and concentrating organisms and as a biological-indicator sensor which measures the organisms' metabolic activity within the membrane (i.e., solid matrix). The concept is based on modifying commercially available microporous membrane filters by incorporating luminescent oxygen-sensitive dye on or into the membrane.

The method for utilizing the Integrated or Dual Biological/Sensors will filter the fluid sample using appropriate filter procedures (e.g., aspiration, gravity, lateral diffusion, etc.). The Biologic/Sensor is placed into a test vessel as described above in BI testing and incubated with the appropriate culture media at the optimal temperature for growth detection. Determination of changes in the oxygen gradient surrounding the solid matrix support containing the microorganisms indicate the presence of microorganisms. This sensing configuration offers the advantage of providing the microenvironment as well as filter capturing of specific sizes of microbes or cells.

This embodiment of the present invention provides a meter or tool to distinguish differences in the numbers of organisms collected from liquid samples. The test also provides a means to detect the outgrowth of organisms much earlier than standard visual detection in tube or plate culture methods. One utility is to assay water samples, and can provide an early warning of the bioburden level in time sensitive process control environments. By the proper choice of the filter membrane pore size, a method of selectively detecting different types of organisms can be achieved. Type identification of specific microbes is an added feature of this design. For example, by using a specific combination of selective growth media, incubation temperature, filter membrane material and filter membrane pore size, a mechanism of selective detection and a semi-quantitative numeration of organisms can be attained. Similar to physical capture of organisms based on pore size exclusion, organisms could be captured within the porous network of filters by the use of biochemical or immunological mechanisms, such as antibody-mediated microbe specific binding methods.

Antimicrobial Drug Sensitivity Testing Method

The present invention further provides a drug sensitivity test device for rapidly determining if a sample of microorganisms are sensitive to a potential antimicrobial therapeutic agent, comprising a plurality of porous solid-matrix support elements, each containing a solid phase luminescent oxygen sensor, and microbial test sample applied to the solid matrix support element; a test vessel containing a solid matrix-support element, growth media, and optionally a potential antimicrobial therapeutic agent. Preferably the solid matrix is selected from cellulosics, mixed cellulose esters, isopore polycarbonate or polyester membranes, nylon filter nets, woven polypropylene, expanded PTFE membranes, and glass fibers mats.

In this embodiment, the device and method provide for testing a microbial isolate for its drug sensitivity/resistance. The diluted isolate can be aliquoted onto a set of integrated sensor disks. The inoculated sensor disks are added to a set of test vessels containing an appropriate culture medium. Different concentrations of the antimicrobial drug are added to the vessels, reserving one vessel as a control (i.e., no drug). The vessels are incubated at the optimal temperature for microbial growth and changes in the luminescent signal from the integrated sensor are monitored from each vessel as a function of time. Differences in the oxygen consumption rate (i.e., luminescent signal) from the control sample are indicative of antimicrobial drug sensitivity/resistance. The device and method further provide for pre-aliquoting the antimicrobial into the integrated disk prior to testing. Sets of pre-aliquoted disks can be provided as a kit.

Example 1

This example illustrates a series of experiments using a prototype solid phase luminescent oxygen sensor and BI test device vessel configuration, as shown in FIG. 1, to assess microorganisms' outgrowth, growth media, assay volumes, and rates of metabolic oxygen consumption in order to optimize the inventive method. In each experiment, B. subtilis was used as the test microorganism, which is a common microbe used for BI sterility-assurance testing. B. subtilis was cultured through two passages from a pure pore suspension product and then diluted in Trypticase Soy Broth (TSY) broth. Serial dilution's were made in the same medium and then loaded into vessels at different concentrations. The microorganism concentrations were determined to be $4 \times 10^7$, $4 \times 10^6$, $4 \times 10^5$, and $4 \times 10^4$ cells/ml, respectively using standard plate-counting methods.

Figures 3A, 3B:
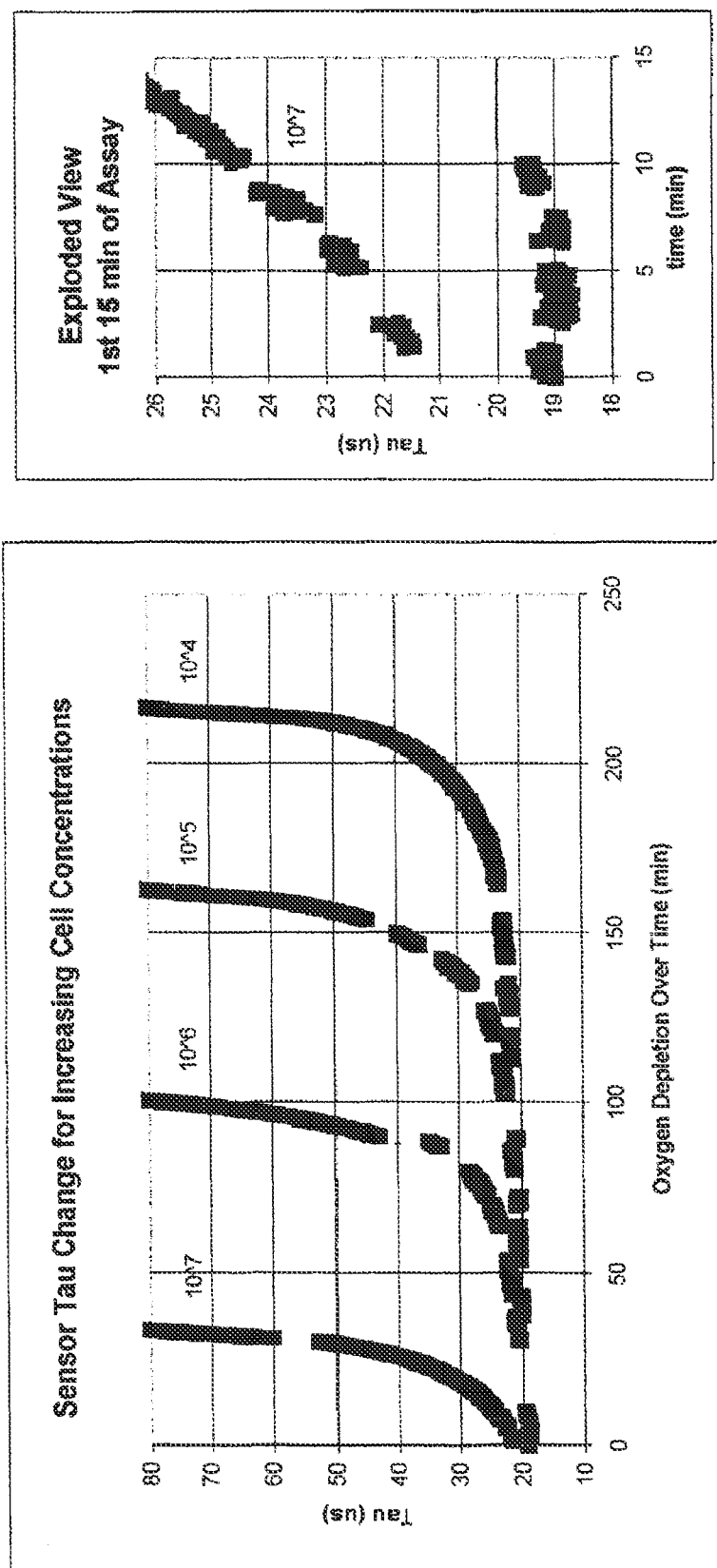
FIGS. 3A and 3B show oxygen depletion curves derived with four BI device vessels containing serial log dilutions of the microorganisms $B.$ $subtilis$ in a TSY growth medium. Oxygen depletion, a measure of the presence of the viable microorganisms, is shown as "tau" which is an increasing phosphorescent lifetime. Baseline tau values of about 20 ms are associated with ambient oxygen levels of ≈6.8 mg/L. The tau measurement plateaus at about 85 ms (not shown) and is associated with a very low level of dissolved oxygen (<0.2 mg/L) indicating nearly complete oxygen consumption. The results show the assay method's ability to track consistent differences in the time course of oxygen consumption in accord with the cell concentration.

The assay samples were not sterilized, but were instead incubated to determine microorganism growth rates. The BI test devices were subject to oxygen sensing at the times indicated in FIG. 3. FIG. 3 shows that an oxygen sensing assay for microorganism growth was, indeed, able to track oxygen metabolism or depletion in the four assay vessels. Each BI test device started with an equivalent oxygen concentration and each ended at the same tau (lifetime) plateau of ~85 microseconds. All of the curves exhibit the same growth pattern, but shifted by time by ~80 minutes between each in a microorganism concentration-dependent manner. At the highest microorganism concentration ($4 \times 10^7$ cells/ml), measurable oxygen consumption was apparent before the optical assay could be started.

Example 2

Figure 4:
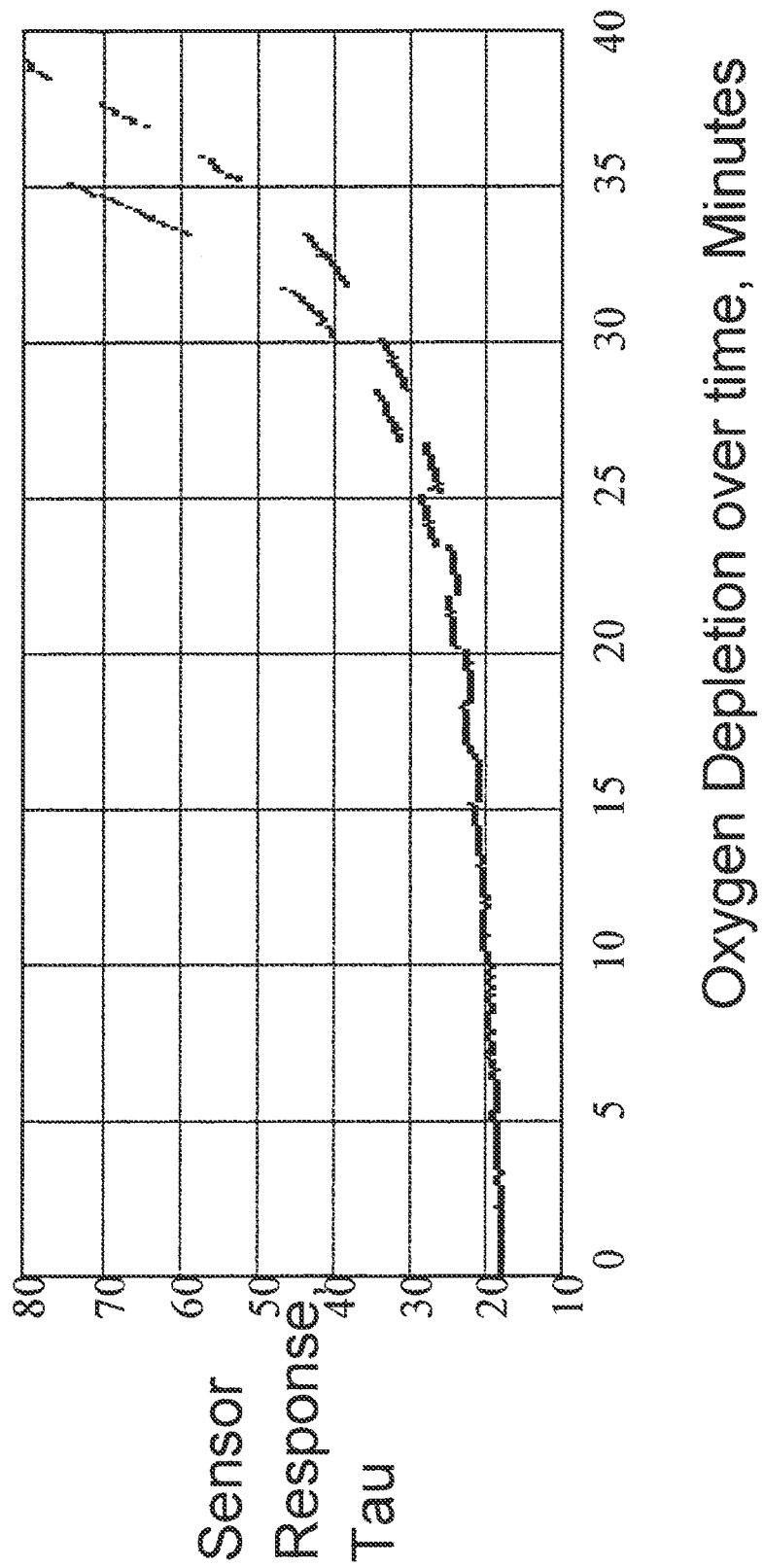
FIG. 4 shows a time course of a bioassay test monitoring two samples of microorganisms differing by only 2% in cell concentration. The co-plots of sensor tau reveals differences between the two samples are resolvable within 10-15 minutes from the assay start with clear distinctions exhibited by 35 minutes.

This example illustrates an experiment wherein very small microorganism population differences were differentiated by measuring microorganism growth using oxygen consumption as a guide. BI test devices were prepared according to the procedures in example 1. FIG. 4 shows a co-tracking tau signal change over time for two samples of B. subtilis microorganisms differing by 2% in cell concentration. Over time, the disparity in oxygen consumption became more pronounced between the different concentrations of microorganisms in the vessels. This experiment was repeated with four sets of microorganism samples, all differing by 2% in cell concentration from one another; and all exhibited distinguishable separable traces in a concentration-dependent manner. Based upon these data, the oxygen sensing method is able to discriminate differences in viable microorganism concentrations down to 1%.

These data were conducted with an early-stage prototype inventive vessel having an assay volume of 1 ml. It should be noted that smaller assay volumes are able to discriminate even smaller differences in viable microorganism concentrations at ever earlier time points. This is because consumption of very small amounts of oxygen result in large changes to dissolved oxygen concentration as the assay volume is decreased.

Example 3

An advantage to the inventive method is assay speed. This example illustrates that in small volumes of assay culture media, changes produced by organisms in the media's oxygen concentration can be quickly identified, thereby reducing the assay time required for detection or measures of microbes' metabolic activity.

Figure 5:
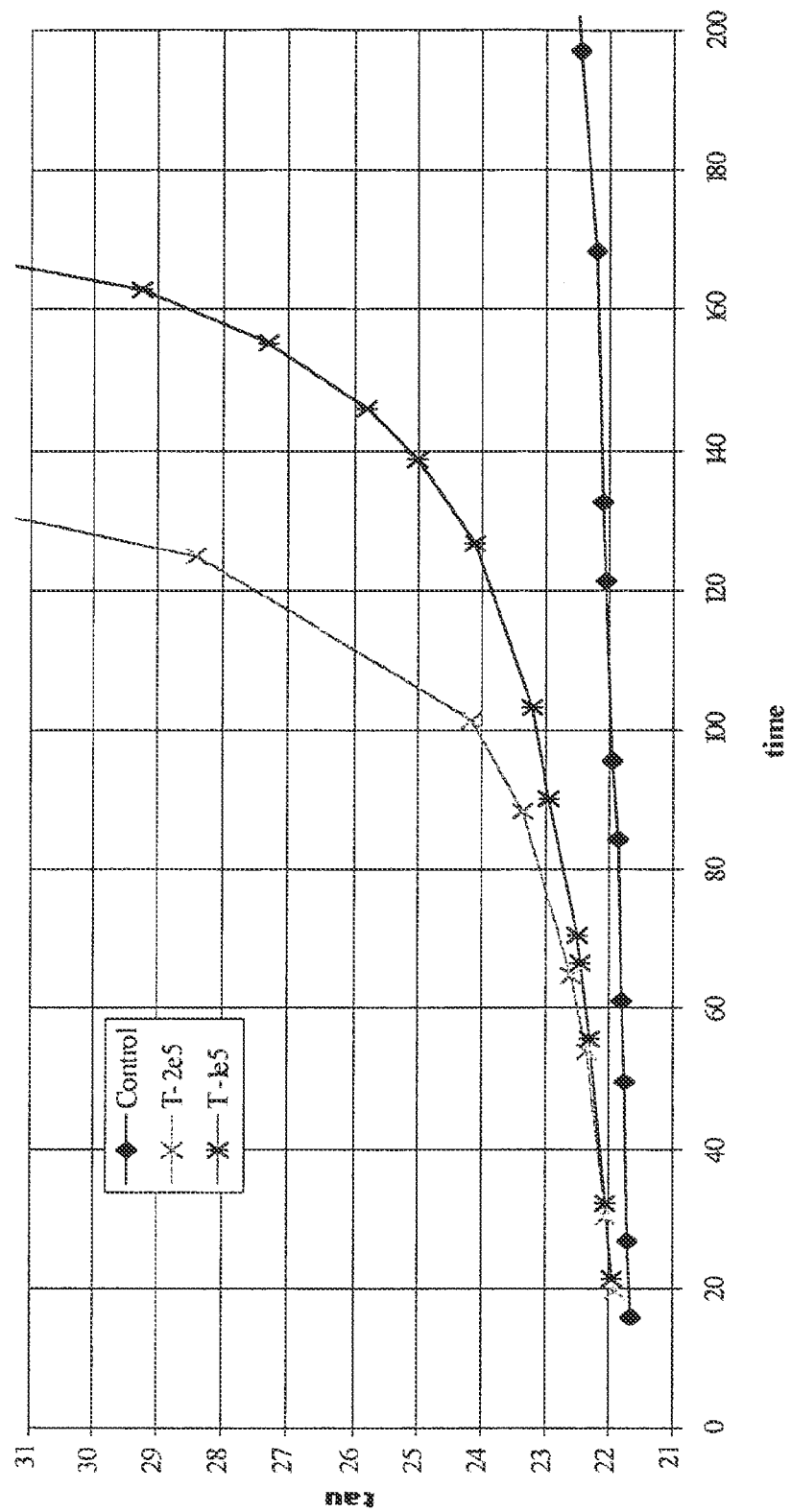
FIG. 5 shows a comparison over a time course (in minutes) for oxygen consumption for 1 or $2\times10^5$ spores as measure by sensor lifetime (tau). Microorganism samples in the form of bacterial spore disks were placed in a BI device vessel and the test was initiated by addition of growth media and capped with sensor tube. The increasing tau over time indicates decreasing dissolved oxygen as microbial metabolism consumes the available oxygen in the growth media.

In this example, the assay media volume was reduced from 1 ml (examples 1 and 2), down to $\leq 100$ μl. Spores of B. subtilis organisms were applied to a solid matrix support, in the form of absorbent paper disks, per the current convention used to prepare spore challenged disks for BI sterility-assurance testing. The disks were placed in BI test type devices, with solid-phase oxygen sensors measuring the oxygen in the culture media, in the manner illustrated in FIG. 2. The results, shown in FIG. 5, tracking oxygen consumption over time in the samples incubated at the 37° C., demonstrate that outgrowth of $1 \times 10^5$ and $2 \times 10^5$ spores can be detected well within one hour, and potentially within 15 minutes. These curves demonstrate both logarithmic and linear consumption regions, indicating both vegetative growth and germination phases, respectively, for these microbial cultures initiated from spores.

Figure 6:
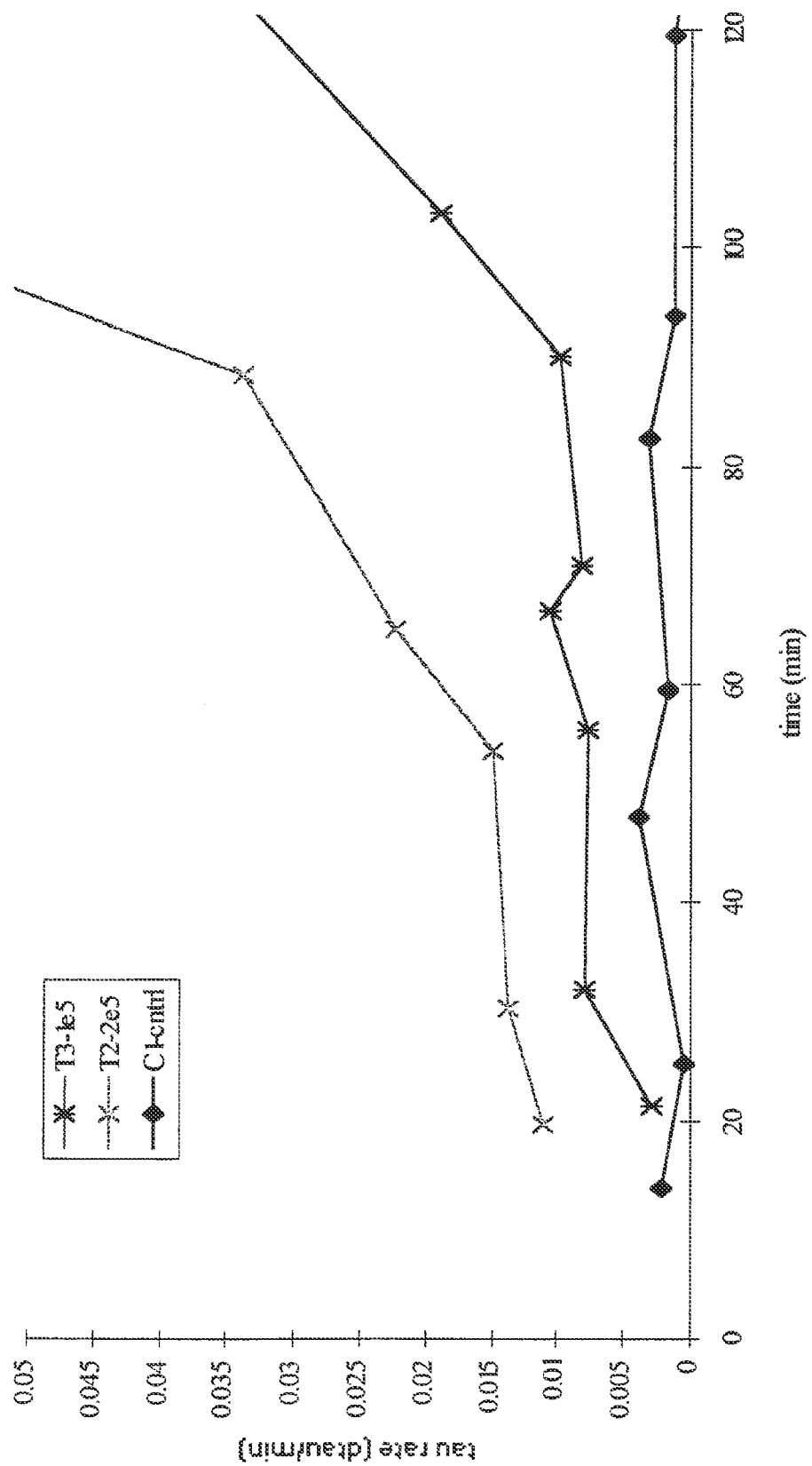
FIG. 6 shows a comparison over a time course (in minutes) for oxygen consumption for 1 or $2\times10^5$ bacterial spores as measured by sensor lifetime (tau) rate of change. The rate of change in tau was calculated for the cultures shown in FIG. 5. The rate of change appears to better detect oxygen consumption associated with different concentration of microorganisms. These data indicate oxygen consumption associated with spore activation of other early metabolic activities.

Simple algorithms can be applied to the data to help enhance early detection of growth. For example, by using a simple derivative filter on the data presented in FIG. 5, one is able to remove any bias in the initial sensor tau values between different sensors without assuming the actual initial oxygen concentration. As shown in FIG. 6, the rate of change of dissolved oxygen concentration showed a difference between $1 \times 10^5$ and $2 \times 10^5$ and the controls even in the initial 30 minutes of the assay.

Example 4

This example presents a model for oxygen consumption by growing microorganism sample populations. It allows a prediction of the effect of reducing the assay-volume on the time-to-positive detection of outgrowth based upon metabolic activity measurements (using the data provided in examples 1 and 2). Table 1 shows projected time-to-positive growth determinations with different assay volumes employed: 1000, 200, and 20 ul. It illustrates that reduction of the assay media volume reduces the time to positive detection. This model assumes the presence of 10 viable microorganisms at the onset of the assay, uses standard assumptions for exponential growth of microorganisms, published values for oxygen content of aqueous solutions, and calculations of oxygen consumption based upon data published for E. coli metabolic rates which are similar to those of B. subtilis: (Backman, J. Biochem. Biophys. Meth. 23:283-93, 1991).

TABLE 1

| | Assay Volume (μl) | | |
| --- | --- | --- | --- |
| | 1000 μl | 200 μl | 20 μl |
| Time to positive detection: | 5.25 hr. | 3.83 hr. | 2.75 hr. |

Example 5

This example demonstrates an ability of the inventive BI test device and method to sense oxygen changes occurring within a limited oxygen-gradient locale (microenvironment) surrounding the microorganism sample. The assay configuration is of the form depicted in FIG. 7, utilizing a Dual Biological/Sensor, i.e. the microorganisms, as spores, applied to one solid-matrix support (spore disk), which rests on top of another support at the bottom of the vessel bearing the solid phase luminescent oxygen sensor. This example, in addition to showing that a dissolved oxygen gradient microenvironment exists around microbial samples in this form, further demonstrates that metabolic activity can be measured in an unsealed BI test device even though the culture medium contents are exposed to air.

BI test device vessels with solid phase luminescent oxygen sensors attached to an optically clear bottom portion were presterilized by steam autoclaving. After sterilizing, microorganisms applied to solid matrix support paper disks (1-2 *B. subtilis* spores) and 1 ml sterile growth media having a pH indicator were added to the test devices. These were incubated at 37° C., while measuring the luminescent signal lifetimes (tau) of the sensor.

Figure 8:
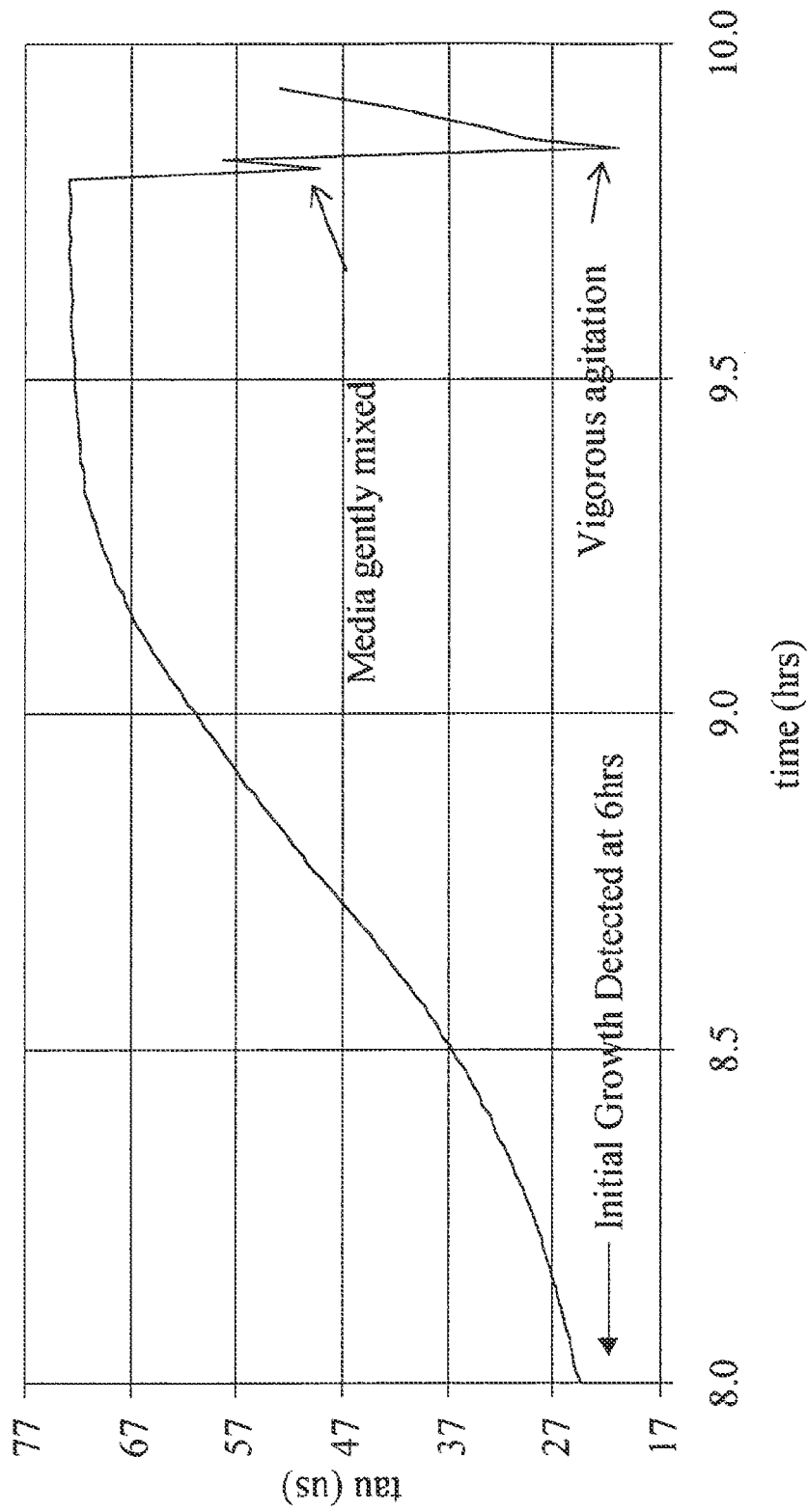
FIG. 8 shows a time course for oxygen consumption (measured as the increase in sensor signal lifetime) for a vessel containing approximately 1 ml of growth media, a spore disk inoculated with 1-2 $B.$ $subtilis$ microorganisms. The spore disk was overlying an optical oxygen sensor (i.e., close proximity). No physical barrier was placed in the vessel and no gas seal was made to protect the growth media from the effects of oxygen ingress from the atmosphere. The test vessel was incubated at 37° C. The results found nearly complete oxygen consumption of the available oxygen in a "microenvironment" located in the region of the spore disk and optical oxygen sensor. When the assay vessel contents were mixed, there were observed significant drops in the oxygen sensor lifetime. These data indicate large differences in oxygen concentration of the growth media located at the microenvironment surrounding the spore disk and the growth media distant from this microenvironment.

After 9.5 hours of incubation, as shown in FIG. 8, the oxygen sensor's luminescent signal lifetime (tau) which initially was about 18 µs had risen to about 75 µs, indicating oxygen consumption and microorganism growth. This change in signal lifetime represents consumption of over 95% of the dissolved oxygen available to the growing microorganisms in the spore disk (i.e., in the microenvironment surrounding the disk and sensor). By contrast, no change in the growth media's visual pH indicator was detectable at this time point in the assay. The test sample was then gently mixed, as indicated on the plot of FIG. 8, which caused a significant drop of the signal lifetime. The result indicates that mixing of the oxygen-depleted media around the microorganism spore disk with media further from it having higher oxygen concentration disturbs and dilutes the oxygen gradient, which is direct evidence for the formation of this microenvironment. More vigorous mixing dropped the signal lifetime to near its starting value, indicating that little net change had occurred in the oxygen content of the bulk of the growth media. Again, without agitation, the sensor lifetime rose back to its pre-mixing levels within a matter of minutes. During this test, no pH indicator change was observed in the growth media until after 26 hours of incubation.

This example indicates a preferred method for performing the oxygen metabolism test. In particular, by placing the microorganisms in close proximity to the optical oxygen sensor, and conducting the assay with growth media in an unstirred volume, the assay can be performed in simple, direct manner without the use of a sealed fluid vessel.

Example 6

In this example, simple methods are demonstrated that minimize sample mixing as might occur due to convection within assay fluid or media contents and potentially to limit the diffusion of oxygen from the bulk solution into a microenvironment surrounding the microorganisms. The assay vessel contained an optical oxygen sensor affixed to the bottom of the assay vessel, microorganisms (approximately 1-2 or $10^4$ spores of *B. stearothermophilus*) administered to absorbent paper disk placed over the optical oxygen sensor and in direct physical contact with the optical oxygen sensor, and a thin-walled glass ampoule containing the growth media (1 ml). After sterilization, the growth media ampoule was crushed, leaving glass shards as a passive barrier to oxygen convection and diffusion to the microenvironment surrounding the microorganisms. For those assay vessels without shards, growth media was added by pipette. The assay vials were incubated at 56° C. (the preferred temperature for *B. stearothermophilus*) and measured continuously for changes in sensor signal lifetime; avoiding mechanical agitation as described in Example 5 above.

Figure 9:
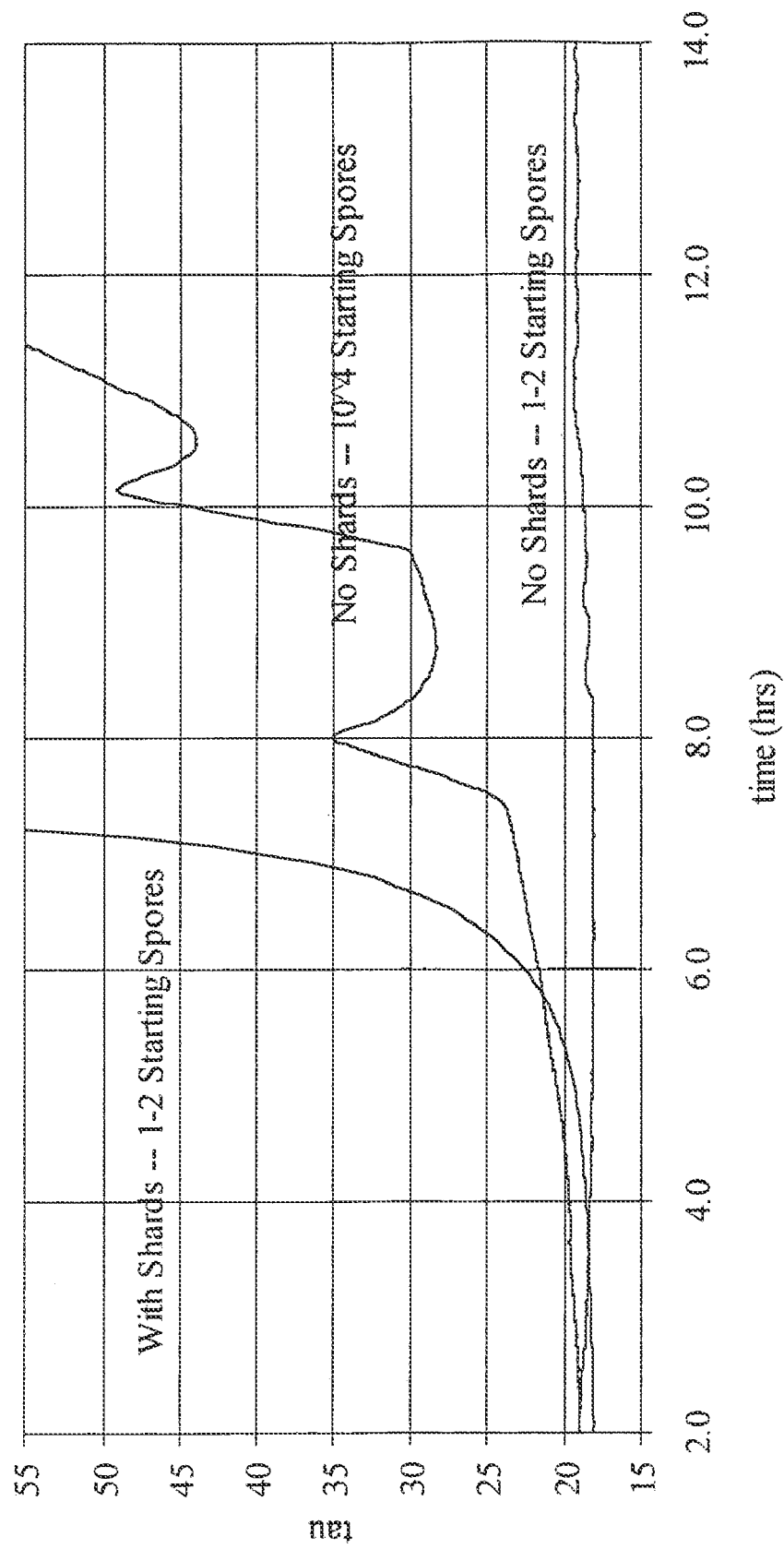
FIG. 9 shows a time course for oxygen consumption (measured as an increase in sensor signal lifetime) for different DI device vessel configurations, each BI device containing approximately 1 ml of growth media, microorganisms fixed onto a solid matrix carrier substrate ("a spore disk") inoculated with either 1-2, or $10^4$ $B.$ $stearothermophilus$ microorganisms, and which is overlying an optical oxygen sensor at the bottom of the BI device vessel. In one configuration, no physical barrier was placed over the spore disk ("No Shards") and in a preferred embodiment, glass shards were introduced into the vessel at the time of media addition, by crushing a sterile glass ampule containing media in the vessel. All of the various BI device vessels were incubated at optimal conditions (37° C.). These data show that the presence of glass shards in the vessel significantly increased local oxygen consumption rate in a microenvironment, as measured by an optical oxygen sensor.

FIG. 9 shows a time course for oxygen consumption (i.e., changes in signal lifetime) for these two vessel configurations (i.e., with and without glass shards) at different microorganism spore concentrations. The assay vessel without glass shards and with only a 1-2 microorganism spore disk showed only transient changes in signal lifetime with no indication of logarithmic growth, as was observed in previous tests. Analogously, an assay vessel with $10^4$ inoculated spores but without any glass shards, eventually consumed the dissolved oxygen content of the growth media within the test volume, however, it approached this state in a discontinuous, "non-characteristic" manner.

In contrast to these observations of discontinuous oxygen consumption curves, the BI assay vessel configuration with glass shards overlying the microorganisms and optical oxygen sensor, showed oxygen consumption curves without discontinuities and more characteristic of a smooth logarithmic growth curve measured in closed vessels. Positive growth was indicated for a viable microorganism sample 1-2 starting spores in less than 4 hours.

These data and those data from example 5 demonstrate that convection and mass transport within the assay vessel growth media can be minimized using physical means, such as baffles or barriers. The glass shards from the media ampoule are a simple and convenient means for introducing such a barrier, however, contrivances specifically designed to provide convection or other mass transport barriers can also be utilized to improve the rapidity of the assay.

Example 7

This example illustrates performance of Integrated Biological Sensors utilized in a shielded assay state with glass shards overlying it. Solid phase luminescent oxygen sensors were prepared by spraying a solution of oxygen sensor dye in a polymeric carrier onto porous solid matrices. Oxygen sensor dye stock solutions were made by dissolving 0.05 gram PtOEP (Porphyrin Products) and 5 grams polycarbonate resin, (Aldrich) in 120 mL of dichloromethane (Aldrich). Adsorbent paper (Schleicher & Schuell) was sprayed with the polymer/sensor dye solution (i.e., a 5% (w/v) with either one or both sides of the paper matrix evenly coating to a density of approximately 1 mg per 10 $cm^2$ per side. The solid phase luminescent oxygen sensor coated paper created was dried overnight, then punched into circular disks of approximately 6 mm diameter, and steam sterilized at 121° C. for 20 minutes.

Integrated biological-sensors were prepared from the sterile punched disks in the following manner. Dilutions of *B. stearothermophilus* spores (AMSCO) were made to four different log concentrations in 40% EtOH/water: $4 \times 10^5$, $4 \times 10^4$, $4 \times 10^3$, and $4 \times 10^2$ spores/ml. From each dilution, 2.5 µl was applied and allowed to adsorb into the disks giving a nominal $10^3$, $10^2$, $10^1$ and $10^0$ organisms entrained per disk, respectively. These integrated biological sensor disks were allowed to dry completely then stored at 4° C. for later use.

To assess outgrowth of the spores, the integrated biological sensor disks were placed in flat-bottomed 8×30 mm (i.d.) polypropylene vessels. A 1 ml glass ampoule containing TSY media, with or without phenol red, was placed into each sample vessel on top of the disk. The vessel was capped and the ampoule crushed, releasing the media into the vessel and saturating the disks. The glass shards from the crushed ampoules helped form a partial barrier to fluid convection. The vessels were incubated at 56° C.±0.2° C. for up to 6 hours in an aluminum dry block. Optical reading was performed as by monitoring oxygen changes in the integrated biological sensor disks' luminescent lifetimes through the bottom of the vessel.

This test configuration was similar to that shown in FIG. 7 and described in Example 6, with the main exception that the spore disk and the sensor were integrated into one physical entity, i.e., the integrated biological sensor design. The oxygen consumption was recorded and prepared for evaluation either as plots of the "luminescent lifetime vs. time" or as the "% Baseline vs. time" (the baseline taken after 30-45 minutes of warm-up and equilibration of the vial and its contents).

Figure 10:
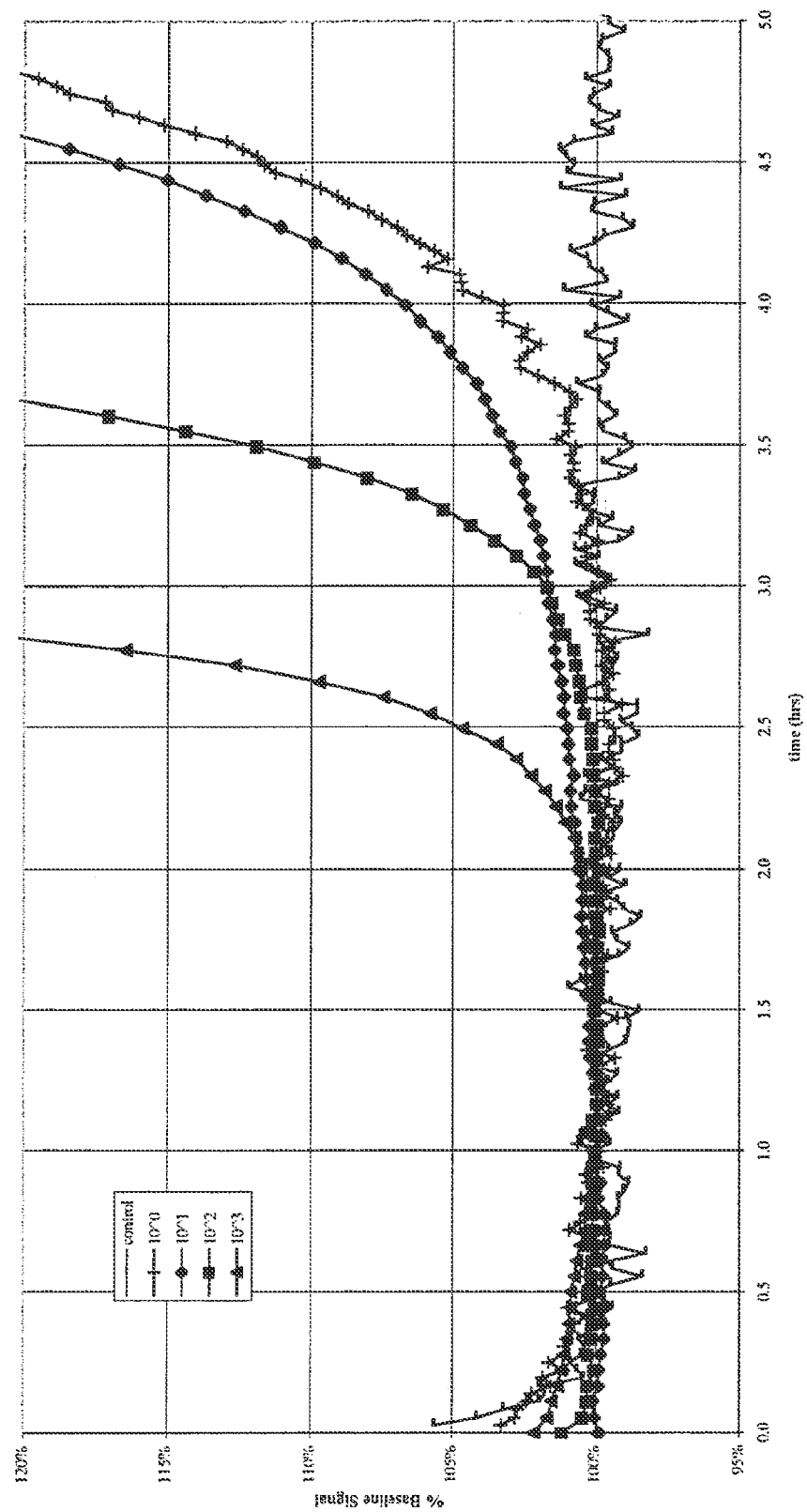
FIG. 10 shows plots of oxygen consumption over time derived from assay of Integrated biological sensors inoculated with various concentrations of $B.$ $stearothermophilus$ spores ranging from $10^3$, $10^2$, $10^1$ and $10^0$. The studies were conducted with glass shards present in the test vessels, overlying the integrated biological sensors.

Typical oxygen consumption curves (% baseline vs. time) for different starting populations of *B. stearothermophilus* are shown in FIG. 10. The results with the integrated biological sensor disks demonstrate significantly faster detection times than in the previous example with the sensor and spore disk in close juxtaposition but separate entities. The time required for the sensor signal lifetime to rise more than 5% above the baseline was used, to determine with a high degree of confidence, the time to outgrowth detection. Based on this detection limit of 105% of baseline, the times to positive grow out for the samples initiated with different numbers of spore were determined as shown in Table 2. The time to positively determine the outgrowth of 1-5 spores (E0) was approximately 4 hrs:20 min, compared to the approximately 5 hrs:10 min growth found with the dual biological sensor approach described in Example 6.

TABLE 2

| Starting Organisms | Time to 105% Baseline (hrs:min) |
|---|---|
| $10^3$ | 2:11 ± 0:08 |
| $10^2$ | 2:43 ± 0:06 |
| >>10 | 3:42 ± 0:34 |
| 1-5 | 4:20 ± 0:25 |

Example 8

This example illustrates results obtained using integrated biological sensor disks in an unshielded assay state, without glass shards present, for comparison and contrast with the previous Example 7 having shards. It shows the importance of the oxygen gradient microenvironment and value of integrated biological sensor design towards providing a more rapid answer in a microbial test situation.

In these tests, integrated biological sensor disks bearing *B. stearothermophilus* spores were placed at the bottom of sample vessels that do not contain glass shards. In addition to placement at the bottom, integrated biological sensor disks were also tested with placement either in the middle or at the top of the culture media fluid-column in vessels with no shards or diffusive barriers present.

To conduct these assessments, integrated biological sensor disks bearing *B. stearothermophilus* spores were prepared as described in Example 7 above. Decreasing log dilutions of *B. stearothermophilus* were made and inoculated to yield final spore concentrations of $10^1$, $10^2$, $10^3$ and $10^4$ spores per integrated biological sensor disk. For the special placement of the disks along the sides of the vial in the middle and at the top of the fluid column, holders were fashioned from thin polypropylene strips >>6×18×0.5 mm in dimension with a gap cut into the strip into which disks were inserted and held the appropriate distance from the bottom of the vessel.

Figure 11:
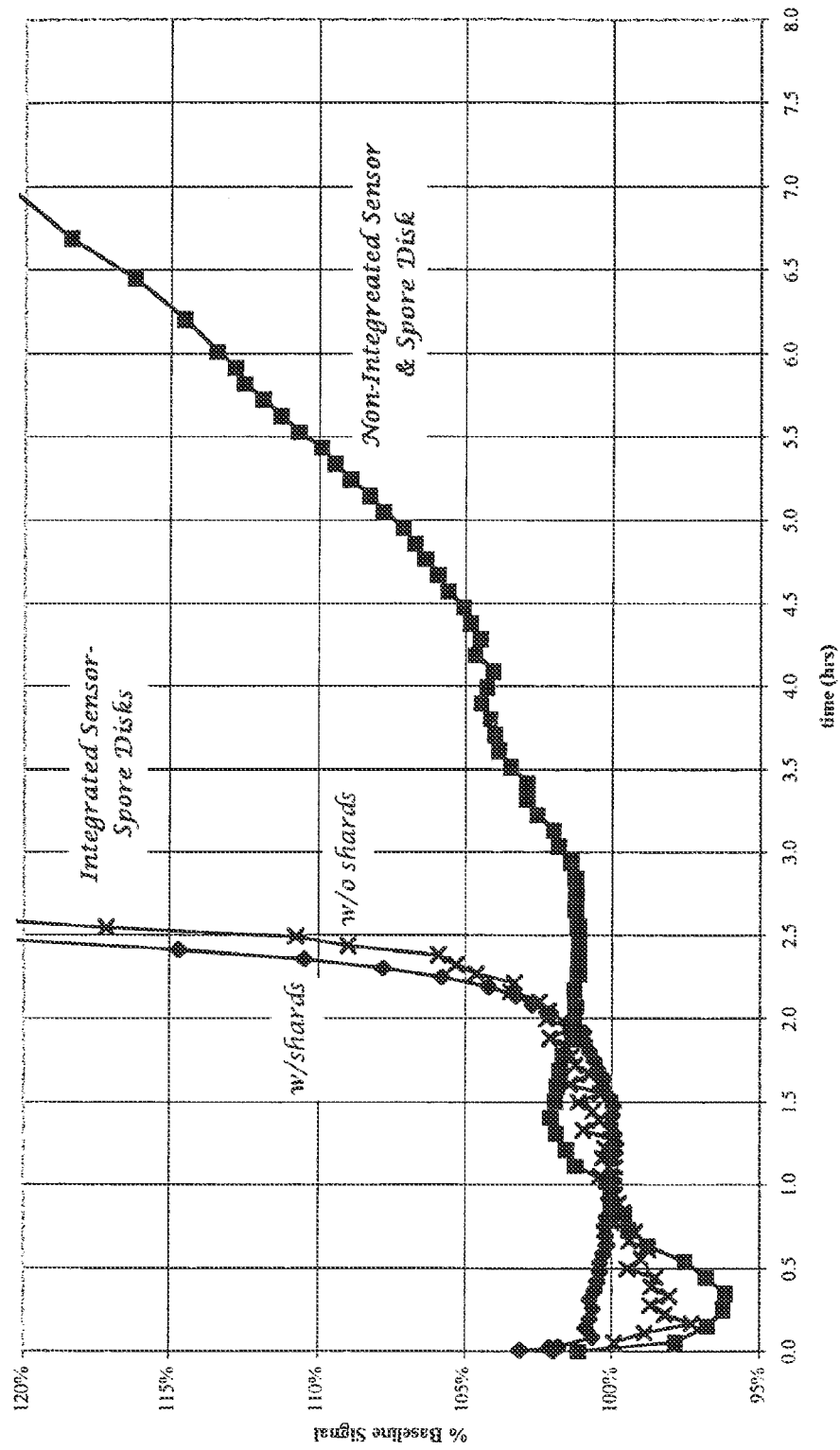
FIG. 11 shows plots of oxygen consumption over time derived from assays of integrated biological sensors inoculated with $10^4$ $B.$ $stearothermophilus$ spores as incubated in vessels under the two conditions with and without shards present. The results indicate that the presence or absence of shards has little or no effect on the performance of integrated biological sensors.

In one set of tests, with the integrated biological sensor disk bearing $10^4$ *B. stearothermophilus* spores placed flat on the bottom of the test vessel, one ml of TSY growth media was added to the test-vessel giving a total fluid column height of approximately 15 mm above it. No glass shards were present. This test sample was incubated at 56° C. and the sensor lifetime signal was monitored using the fiberoptic instrument described in Example 1. The results are to be compared to a similar test using $10^4$ spores per disk but with the glass shards of a crushed media ampoule present as described in Example 7. The results, shown in FIG. 11B, demonstrate that with use of the integrated biological sensor, there is no significant difference between the tests with or without shards present. As a further comparison, the results of the non-integrated, dual biological sensor testing described in Example 6, are shown in FIG. 11B. In addition to the much faster detection time for the integrated biological sensor design, the discontinuities observed in FIG. 6 are not apparent.

For the more rigorous testing of the integrated biological sensor and demonstration of its utility, assays were conducted with the inoculated disks bearing either $10^3$, $10^2$, and $10^1$ spores per disk, as held by the polypropylene strips in the middle of the fluid column approximately 7 mm from the bottom of the vessel. Additionally, the integrated biological sensor was tested bearing $10^4$ spore as held at the top of the 15 mm TSY media fluid column in test vessels. In the latter case, approximately ¼ of the disk was exposed to air. After initiation of the cultures by incubating at 56° C., the samples were read through the side of the vessel using adaptation of the fiber optic based instrument described previously.

Figure 12:
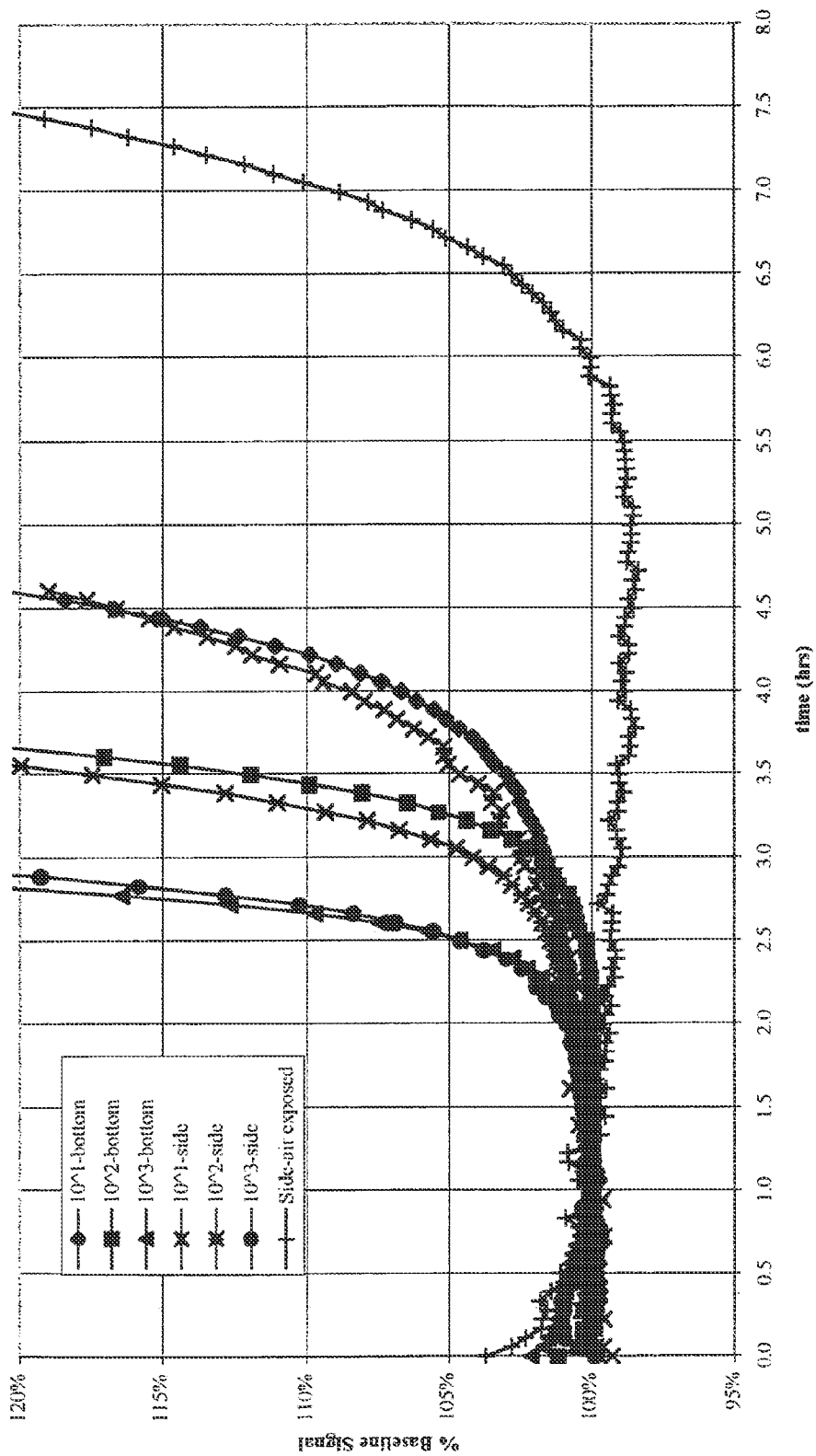
FIG. 12 shows plots of oxygen consumption over time derived from assay of integrated biological sensors inoculated with various concentrations of $B.$ $stearothermophilus$ spores as incubated in vessels without shards present. The integrated biological sensors were held in place at different positions within fluid column formed by the culture media in order to assess convection effects upon the oxygen gradients formed by the growing organisms around the integrated biological sensors.
Figure 13:
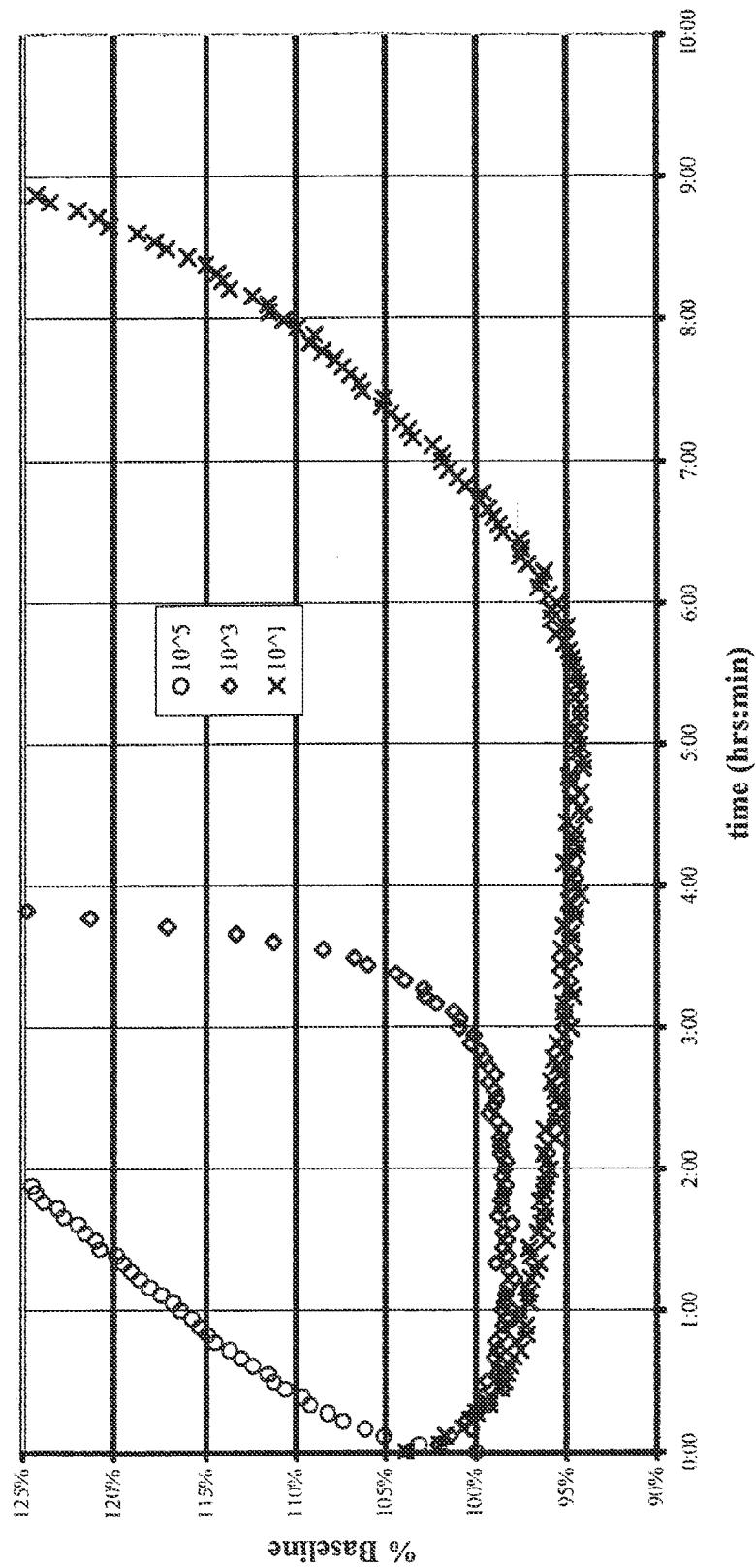
FIG. 13 shows plots of oxygen consumption over time derived from assay of integrated biological sensors employed as filters collecting microorganisms from fluid samples passed through them. Liquid samples containing $10^5$, $10^3$, or $10^1$ actively growing $B.$ $subtilis$ organisms were filtered through integrated biological sensors made from glass-fiber filter mats. The results indicate that the oxygen consumption measurements from the incubated filter devices correlate in a concentration dependent manner with the microbial content of the contaminated liquid samples.

FIG. 12 shows oxygen consumption curves for the samples held in the various positions. The results from Example 7 are co-plotted to enable the comparison with integrated biological sensors that were tested as placed lying on the bottom of the vessel with glass shards present. The results demonstrate that, for all of the test samples submersed in fluid, there is no significant difference in the time to detection for any of the spore concentrations tested with utilization of the integrated biological sensors as placed either at the bottom or held in the middle of the fluid column. Moreover, the presence or absence of the glass shards makes no difference. This indicates that what is being sensed is the oxygen gradient created within the microenviroment of the integrated biological sensor itself by the growing organisms' consumption of oxygen; rather than oxygen in the bulk fluid at large, since convection should be greater for samples held in the middle of the fluid column compared to the bottom, and otherwise should have caused a slower rate of oxygen change.

Consistent with this interpretation, the integrated biological sensors at the top of the fluid column, even though partially exposed to ambient air, were nonetheless able to demonstrate oxygen consumption after approximately 6 hours of incubation, well before any indication of growth was observed by the pH indicator in the media.

Example 8

This example illustrates the use of an integrated biological sensor as a porous membrane device for general detection of metabolizing microorganisms. In this example, the integrated sensor was designed to function both as a filter membrane device for capturing and concentrating microorganisms and as a oxygen sensor which measures the organisms' metabolic activity within the membrane microenvironment. A commercially available microporous membrane filter was modified by incorporating an oxygen sensor thin film on or into the membrane. Liquid samples containing microorganisms were filtered through the membrane having small pores that retain the microbial organisms. The integrated filter sensor membrane was incubated with the appropriate culture media at a chosen temperature. This sensing configuration offered the advantage of providing a microenvironment as well as a filter, capable of capturing specific sizes of microbes or cells.

Filter sensor membranes were prepared as follow: Sensor stock solution was made by dissolving 0.05 gram PtOEP, (Porphyrin Products, lot #021690) and 5 grams polycarbonate resin, (Aldrich 18, 162-5) in 120 ml of dichloromethane (Aldrich). Integrated sensors were made by spraying the sensor stock solution onto Millipore AP-40 glass-fiber filters with a 0.7 mm pore size (lot #H4BM01258). The process used an airbrush (Baasch model H) sprayer driven with dry nitrogen gas tank with the brush nozzle kept 15 cm from the filter paper surface. Sprayed filters were dried overnight at room temperature. Integrated filter sensor disks, 0.25 inches in diameter, were punched from the sprayed filter preparations. Disks were steam sterilized for 30 minutes at 121° C. before use.

To harvest organisms, filter-sensor disks were placed on a vacuum pad of a Milliflex filtration system (Millipore). Separate 1 ml solutions of $10^1$, $10^3$ and $10^5$ B. subtilis organisms in suspension were suctioned through the disks. To culture the organisms caught, the disks were placed into sterilized polypropylene vials with 1 ml of Trypticase Soy Broth media (BBL lot #15CJVD). The vials were loosely capped and incubated at 32° C.±1° C. in a heater block that enabled optical reading and tracking of the integrated sensors' luminescent signals through the bottom of the vessels, similar to FIG. 7.

Results of the continuous oxygen level measurements of the grow out of the three filtered water samples are shown in FIG. 10. The % signal level change was indicative of the oxygen level changes such that a higher % signal is proportional to lower oxygen concentration which in turn is indicative of oxygen consumption activity. The $10^5$ B. subtilis filtered sample shows a rapidly changing oxygen level from the very beginning of the assay. It required 3 hrs: 30 min. for the $10^3$ sample to rise more than 5% above baseline; and over 6 hours for the $10^1$ sample to show appreciable % signal change. These results can be compared to those for B. subtilis organisms growing in suspension in a 1 ml volume, as described in Example 1. They indicate that the integrated filter-sensors can capture the organisms in a fluid sample and assess metabolic activity of the entrained organisms in a concentration dependent manner. Moreover, as expected, the oxygen consumption registered for a given concentration of organisms is higher when they are trapped at the level of the sensor than when they are dispersed in a bulk fluid sample (such as in Example 1).

The test therefore provided a meter or tool to distinguish differences in the numbers of organisms present in the liquid samples. The test also provided a means to detect the outgrowth of organisms much earlier than standard visual detection in tube or plate culture methods.

Example 10

This example demonstrates the integrated sensor-BI method's utility and advantage in terms of improved speed in determining the susceptibility, or resistance, of a microbial population to an antibiotic. In this example, organisms were applied to the integrated biological sensor disk in order to attain rapid measures of activity within the disk's microenvironment while the disk was incubated in culture media containing the antibiotic being assayed for effects on the microbial population.

B. subtilis organisms were cultured in Trypticase Soy Broth (TSB) media to obtain an inoculum of actively growing test organisms. Twenty microliter aliquots, each containing 400,000 cells (established by subsequent plate counting), were removed, and dispensed onto 0.25 inch diameter dry oxygen-sensor disks prepared from 0.45 micron pore cellulose-ester filter membrane stock (Millipore), in a manner similar to that described in Example 7. These integrated biological sensor disks bearing organisms were placed at the bottom of sterile polypropylene vessels, to which was added 1 ml of TSB media containing penicillin at concentrations of 5 ug/ml, or 5 ng/ml, or no antibiotic in the case of the positive growth control.

Alternatively, as a comparison of outgrowth and detection of antibiotic effects under bulk-volume assay conditions, identical aliquots of B. subtilis organisms were and mixed into 1 ml samples of TSB media prepared with and without penicillin as described above and dispensed into vessels. To measure oxygen consumption of the organisms in these bulk suspension samples, oxygen-sensor disks of the same derivation as the above integrated sensors, but without organisms applied to them, were placed in the bottom of the vessels.

All samples were prepared and cultured in parallel, incubated at 37° C. and the oxygen consumption tracked via the integrated sensors' luminescent signals, in a manner similar to that shown in FIG. 7. The signal plots revealed that the integrated biological sensor control sample registered definitive outgrowth of the applied B. subtilis organisms within 45 minutes of initiating the assay, i.e. exhibited a 5% rise above its equilibrated state baseline signal at 15 minutes into assay and was increasing rapidly. The inhibitory effect of penicillin on organisms' growth was already manifesting itself in this time frame. After 60 minutes of assay, the control sample without penicillin had a 12% signal increase whereas the samples exposed to a low dose of 5 ng/ml penicillin, although metabolically active, were indicating measurable inhibition showing only a 6% signal increase. At the higher penicillin dose, 5 ug/ml, the cells in the integrated BI exhibited no evidence of metabolic activity, and continued to show no activity throughout 40 hours of monitoring the samples. These data indicate that the B. subtilis organisms were, indeed, sensitive to penicillin.

By comparison, the bulk volume cultures of B. subtilis after 60 minutes were just beginning to show indications of growth but were too early into the assay to identify inhibitory effects. The control, without antibiotic present, was just 2% above baseline, which was the same signal level as the 5 ng/ml penicillin sample. The 5 ug/ml high dose registered 1% above baseline. The bulk sample control lagged behind the integrated-sensor BI control, requiring about an hour of additional incubation, or twice as long, to attain equivalent signal change (12%) as the integrated sample showed at 60 minutes.

A similar companion study, indicated the potential of the integrated sensor-BI to detect microbial activity and identify antibiotic sensitivity in several hours, using a small number of organisms to initiate the test. Inoculum of only 8,000 B. subtilis cells were collected by filtration, similar to Example 9, on oxygen-sensor disks made from Millipore AP-40 glass-fiber filter material (0.7 micron particle retention). In about 3.5 hours, without antibiotic present, the population expanded in the integrated biological sensor control, producing a 5% level signal increase, i.e. positive indication of outgrowth. Inhibition was demonstrated in both integrated biological sensor samples exposed to penicillin at 5 ng/ml and 5 ug/ml. No signal change was measurable at this time point. After 8 hours of incubation, the low-dose penicillin exposed population eventually expanded enabling assay detection of outgrowth. No activity was identified in the sample exposed to the high dose at any point over the 20 hour assay.

The test results additionally indicate, based on the differential antibiotic concentration-dependent response, that using the times to growth detection, the inhibitory effects of the antibiotic can be estimated similar to a MIC assay, by employing a variety of antibiotic dilutions. Moreover, the example serves to illustrate how the oxygen-sensor based assay can be utilized to generally test for agents effecting cells' metabolism: to either test the effect of various agents' on indicator cells; or test the sensitivities of cells' to different agents.

We claim:

1. An optical sensor component, for Biological Indicator (BI) testing or drug resistance/sensitivity testing, comprising a porous matrix containing within it or layered on it, a solid phase luminescent oxygen sensor and microorganisms, and optionally containing a potential antimicrobial drug, wherein the solid phase luminescent oxygen sensor comprises a luminescent oxygen sensor dye within a polymeric carrier.

2. The integrated optical sensor component of claim 1, wherein the luminescent oxygen sensor dye is selected from the group consisting of a polycyclic aromatic hydrocarbon, a longwave absorbing dye, a heterocycle, a porphyrin, a ruthenium(II)tris(bipyridyl) complex, an osmium(II)tris(bathophenanthroline) complex, and a combination thereof.

3. The integrated optical sensor component of claim 1 wherein the porous matrix is at least one selected from the group consisting of cellulosic materials, mixed cellulose esters, isopore polycarbonate, polyester membranes, nylon filter nets, woven polypropylene, expanded polytetrafluoroethylene (PTFE) membranes, glass fiber filter, filter paper, and a combination thereof.

4. A drug resistance/sensitivity test device for rapidly determining if a sample of microorganisms is resistant or sensitive to a potential antimicrobial therapeutic agent, comprising:
(a) a plurality of porous solid matrix elements, each containing a solid phase luminescent oxygen sensor and a sample of microorganisms, both applied to or contained within the porous solid matrix element; and
(b) a test vessel containing the porous solid matrix elements, growth medium, and optionally a potential antimicrobial therapeutic agent, wherein the porous solid matrix element is an absorbent or filtering device.

5. The drug resistance/sensitivity test of claim 4, wherein, in each case, the porous solid matrix element is selected from the group consisting of cellulosic materials, mixed cellulose esters, isopore polycarbonate or polyester membranes, nylon filter nets, woven polypropylene, expanded polytetrafluoroethylene (PTFE) membranes, glass fiber filter, filter paper, and a combination thereof.

6. A microbial activity test device for rapidly determining microbial activity in a filtered sample of microorganisms, comprising:
(a) a porous solid matrix element, containing a solid phase luminescent oxygen sensor applied to or contained within the matrix element, and a potentially contaminated sample filtered through the solid matrix element; and
(b) a test vessel containing the solid matrix element and growth medium, wherein the porous solid matrix element is an absorbent or filtering device.

7. The microbial activity test device of claim 6, wherein the porous solid matrix element is selected from the group consisting of cellulosic materials, mixed cellulose esters, isopore polycarbonate, polyester membranes, nylon filter nets, woven polypropylene, expanded polytetrafluoroethylene (PTFE) membranes, glass fiber filter, filter paper, and a combination thereof.

8. An optical-assay system for determining oxygen content in a vessel, comprising:
(a) an optical sensor component, comprising a porous solid matrix containing within or layered on, a solid phase luminescent oxygen sensor and microorganisms, wherein the solid phase luminescent oxygen sensor comprises a luminescent oxygen sensor dye within a polymeric carrier, and, when irradiated with light of an appropriate wavelength, generates a returned luminescent signal;
(b) a light source that irradiates the solid phase luminescent oxygen sensor;
(c) a photodetector device that monitors the returned luminescent signal and processes the returned signal into a measure of relative oxygen concentration; and
(d) a means for transmitting irradiating light to the solid phase luminescent oxygen sensor and for transmitting the returned signal from the solid phase luminescent oxygen sensor to the photodetector device.

9. The optical assay system of claim 8 wherein the optical assay system is used for biological oxygen demand (BOD) testing, providing that contents in the vessel are mixed.

10. The optical assay system of claim 9 wherein the solid phase luminescent oxygen sensor is affixed to a cap of a BOD testing vessel.

11. The optical assay system of claim 8, wherein the solid phase luminescent oxygen sensor is contained within or layered on the porous solid matrix along with microorganisms.

12. The integrated optical sensor component of claim 1, wherein the polycyclic aromatic hydrocarbon is pyrene, pyrenebutyric acid, fluoranthene, decacyclene, diphenylanthracene or benzo(g,h,i)perylene.

13. The integrated optical sensor component of claim 1, wherein the longwave absorbing dye is perylene dibutyrate.

14. The integrated optical sensor component of claim 1, wherein the heterocycle is fluorescent yellow or tyrpaflavin.

15. The integrated optical sensor component of claim 1, wherein the porphyrin is a platinum octaethylporphyrin, palladium octaethylporphyrin, tetraphenylporphyrin, tetrabenzoporphyrin, chlorin, bacteriochlorin, isobacteriochlorin or chlorophyll.

16. The integrated optical sensor component of claim 1, wherein the polymeric carrier is selected from the group consisting of polycarbonate, silicone, polymethyl methacrylate, polystyrene, polyvinylchloride, and alpha-methyl styrene.

17. A method for rapidly assessing the oxygen metabolism of a sample of microorganisms, comprising:
(a) obtaining an optical sensor component, for biological indicator (BI) testing or drug resistance and/or sensitivity testing, comprising a porous solid matrix containing within it or layered on it, a solid phase luminescent oxygen sensor and microorganisms, wherein the solid phase luminescent oxygen sensor comprises a luminescent oxygen sensor dye within a polymeric carrier;
(b) irradiating the solid phase luminescent oxygen sensor to create a returned luminescent signal; and
(c) measuring and processing the returned luminescent signal into a measure of relative oxygen concentration within a surrounding oxygen gradient.

18. The method of claim 17, wherein the microorganisms are contained within the porous solid matrix component.

19. The method of claim 17, wherein the solid phase luminescent oxygen sensor is layered on the porous solid matrix.

20. A biological indicator (BI) test device, comprising:
(a) a vessel having internal contents and a barrier to external contamination of the vessel internal contents, wherein a portion of the vessel provides for optical interrogation of the internal contents of the vessel, wherein the internal contents of the vessel comprise
(b) an optical sensor component, for biological indicator (BI) testing or drug resistance and/or sensitivity testing, the optical sensor comprising a porous solid matrix containing within it or layered on it, a solid phase luminescent oxygen sensor and microorganisms, wherein the solid phase luminescent oxygen sensor comprises a luminescent oxygen sensor dye within a polymeric carrier; and (c) a growth medium capable of sustaining growth of the microorganisms and containing measurable quantities of oxygen.

21. The BI test device of claim 20, wherein the solid phase luminescent oxygen sensor is contained on the surface of the porous solid matrix.

22. The BI test device of claim 20, wherein the microorganisms are contained within the porous solid matrix.

23. The BI test device of claim 20, wherein the microorganisms comprise viable bacterial spores.

24. The BI test device of claim 23, wherein the bacterial spores comprise spores of Bacillus stearothermophilus or Bacillus subtilis or a combination thereof, for sterility assurance testing.

25. The BI test device of claim 20, wherein the porous solid matrix comprises a material selected from the group consisting of cellulosic materials, mixed cellulose esters, isopore polycarbonate, polyester membranes, nylon filter nets, woven polypropylene, expanded polytetrafluoroethylene (PTFE) membranes, glass fiber filter, filter paper, and a combination thereof.

26. The BI test device of claim 20, wherein the polymeric carrier comprises a material selected from the group consisting of polycarbonate, silicone, polymethyl methacrylate, polystyrene, polyvinylchloride, alpha-methyl styrene, and a combination thereof.

27. The BI test device of claim 20, wherein the luminescent oxygen sensor comprises a dye selected from the group consisting of: a polycyclic aromatic hydrocarbon; a longwave absorbing dye; a heterocycle; a porphyrin; a ruthenium(II)tris (bipyridyl) complex; an osmium (II)tris(bathophenanthroline) complex; and a combination thereof.

28. The BI test device of claim 20, wherein the BI test device comprises a physical or chemical barrier to retard ingress of oxygen to the microorganisms.

29. The BI test device of claim 20, wherein the growth medium is contained within an enclosed glass vessel that can be broken to deliver the growth medium to the microorganisms.

30. The integrated optical sensor component of claim 27, wherein the polycyclic aromatic hydrocarbon is pyrene, pyrenebutyric acid, fluoranthene, decacyclene, diphenylanthracene or benzo(g,h,i)perylene.

31. The integrated optical sensor component of claim 27, wherein the longwave absorbing dye is perylene dibutyrate.

32. The integrated optical sensor component of claim 27, wherein the heterocycle is fluorescent yellow or tyrpaflavin.

33. The integrated optical sensor component of claim 27, wherein the porphyrin is a platinum octaethylporphyrin, palladium octaethylporphyrin, tetraphenylporphyrin, tetrabenzoporphyrin, chlorin, bacteriochlorin, isobacteriochlorin or chlorophyll.

34. A method for biological indicator (BI) testing for determining the effectiveness of a sterilization cycle, comprising:

(a) exposing a biological indicator test device to a sterilization cycle, wherein the BI test device comprises (i) a vessel having internal contents and a barrier to external contamination of the vessel internal contents, wherein a portion of the vessel provides for optical interrogation of the internal contents of the vessel, wherein the internal contents of the vessel comprise (ii) an optical sensor component, for biological indicator (BI) testing or drug resistance and/or sensitivity testing, the optical sensor comprising a porous solid matrix containing within it or layered on it, a solid phase luminescent oxygen sensor and microorganisms, wherein the solid phase luminescent oxygen sensor comprises a luminescent oxygen sensor dye within a polymeric carrier, and wherein the internal contents comprise (iii) a growth medium capable of sustaining growth of the microorganisms and containing measurable quantities of oxygen;

(b) exposing the microorganisms to the growth medium, and incubating the biological indicator test device under incubation conditions suitable for growth of the microorganisms; and (c) determining the oxygen consumption within the BI test device, over a time interval, wherein evidence of oxygen consumption indicates the presence of surviving microorganisms and incomplete sterilization.

35. The method for BI testing of claim 30, wherein the time for incubation is at least 20 minutes but no longer than 16 hours under optimal growth conditions for the microorganisms.

36. A method for antimicrobial agent resistance and or sensitivity testing of a potentially contaminated sample, comprising:

(a) providing a drug resistance and/or sensitivity test device, wherein the drug resistance and/or sensitivity test device comprises (i) an optical sensor component, for biological indicator (BI) testing or drug resistance and/or sensitivity testing, comprising a plurality of porous solid matrix elements, each containing a solid phase luminescent oxygen sensor applied to or contained within the porous solid matrix element, wherein the solid phase luminescent oxygen sensor comprises a luminescent oxygen sensor dye within a polymeric carrier, wherein the porous solid matrix element comprises an absorbent or filter;

(b) administering a sample potentially contaminated with microorganisms to the porous solid matrix elements;

(c) exposing one porous solid matrix element separately in each of a respective plurality of test vessels, each test vessel containing a growth medium and at least one test vessel containing a potentially antimicrobial therapeutic agent;

(d) incubating each test vessel under conditions suitable for microbial growth; and (e) determining the oxygen consumption within the test vessels, over a time interval, wherein evidence of oxygen consumption in the test vessels containing growth medium with the potential antimicrobial therapeutic agent indicates the presence of viable microorganisms resistant to the potential antimicrobial therapeutic agent, and wherein absence or reduced oxygen consumption indicates microbial sensitivity to the potential antimicrobial therapeutic agent.

37. A method for determining microbial activity in a potentially contaminated sample, comprising:

(a) providing a microbial activity test device, wherein the microbial activity test device comprises (i) an optical sensor component, comprising a porous solid matrix element, containing within it or layered on it, a solid phase luminescent oxygen sensor, wherein the solid phase luminescent oxygen sensor comprises a luminescent oxygen sensor dye within a polymeric carrier, and wherein the porous solid matrix element comprises an absorbent or filtering device;
(b) filtering a potentially contaminated sample through the porous solid matrix element to provide an integrated optical sensor component;
(c) exposing the integrated optical sensor component in a test vessel containing a growth medium to the potentially contaminated sample;
(d) incubating the test vessel under conditions suitable for microbial growth; and
(e) determining the oxygen consumption within the test vessel, over a time interval, wherein evidence of oxygen consumption indicates the presence of viable microorganisms.

* * * * *